United States Patent [19]

Wiegers et al.

[11] Patent Number: 5,241,089

[45] Date of Patent: Aug. 31, 1993

[54] POLYHYDRODIMETHYLNAPHTHALENE SPIROFURAN DERIVATIVES, ORGANOLEPTIC USES THEREOF AND PROCESS FOR PREPARING SAME

[75] Inventors: Wilhelmus J. Wiegers, Red Bank; Marie R. Hanna, Keyport, both of N.J.

[73] Assignee: International Flavors & Fragrances Inc., New York, N.Y.

[21] Appl. No.: 22,936

[22] Filed: Feb. 26, 1993

Related U.S. Application Data

[62] Division of Ser. No. 965,698, Oct. 23, 1992.

[51] Int. Cl.$^5$ .......................................... C07D 307/77
[52] U.S. Cl. .................................. 549/299; 562/510; 568/819
[58] Field of Search ............... 562/510; 549/298, 299; 568/819

[56] References Cited

U.S. PATENT DOCUMENTS

| | | | |
|---|---|---|---|
| 3,045,028 | 7/1962 | Enninga et al. | 260/346.2 |
| 3,281,432 | 10/1966 | Blumenthal et al. | 260/346.2 |
| 3,417,107 | 12/1968 | Chodroff et al. | 260/346.1 |
| 4,010,286 | 3/1977 | Hall et al. | 426/536 |
| 4,639,330 | 1/1987 | Sprecker et al. | 252/522 R |
| 4,677,233 | 6/1987 | Buchi et al. | 568/819 |
| 5,196,613 | 3/1993 | Naegeli | 568/819 |

OTHER PUBLICATIONS

Ohloff et al, Chem. Abstr., vol. 85, #94525e (1970).
Jacobson, et al, Tetrahedron Letters, vol. 21, pp. 1205-1208, (1980), title "Three Carbon Annelation Reagents: Unsaturated Alpha Aminonitriles as Homoenolate Equivalents".

*Primary Examiner*—James H. Reamer
*Attorney, Agent, or Firm*—Arthur L. Liberman

[57] ABSTRACT

Described are polyhydrodimethylnaphthalene spirofuran derivatives defined according to the generic structure:

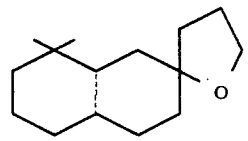

wherein the dashed line represents a carbon-carbon single bond or a carbon-carbon double bond a process for preparing same and uses thereof in augmenting, enhancing or imparting an aroma in or to perfume compositions, colognes and perfumed articles including but not limited to solid or liquid, anionic, cationic, nonionic or zwitterionic detergents, fabric softener compositions, fabric softener articles and hair preparations.

3 Claims, 14 Drawing Sheets

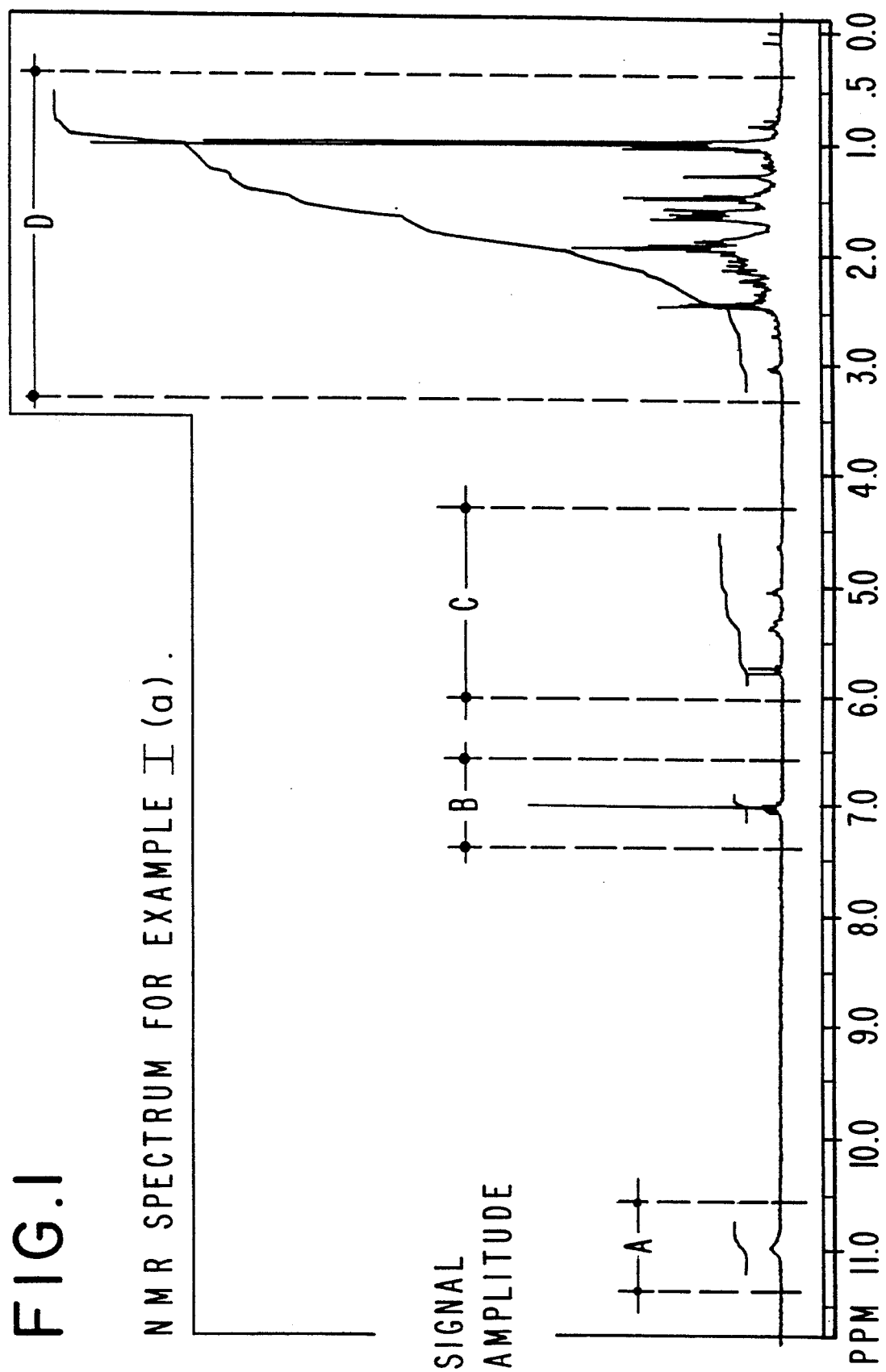

FIG.I-A
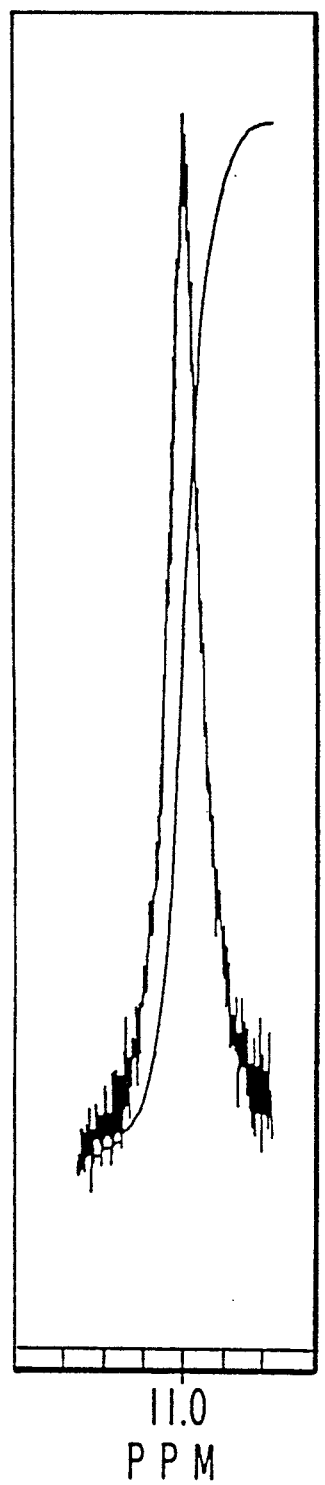
11.0
PPM
FIG.I-B
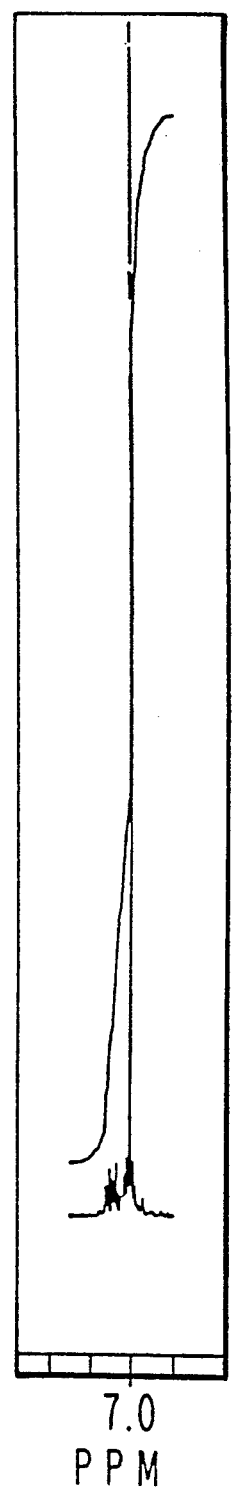
7.0
PPM

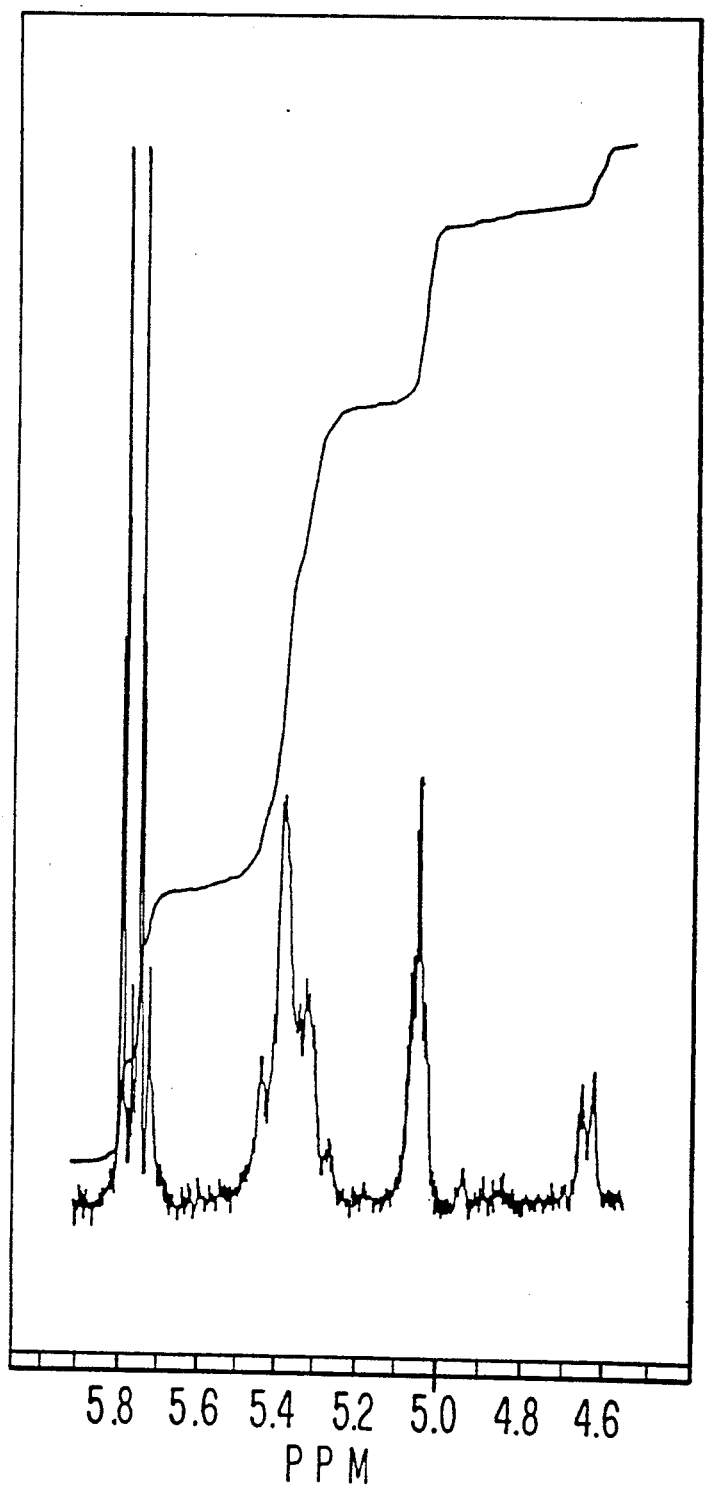
FIG.1-C

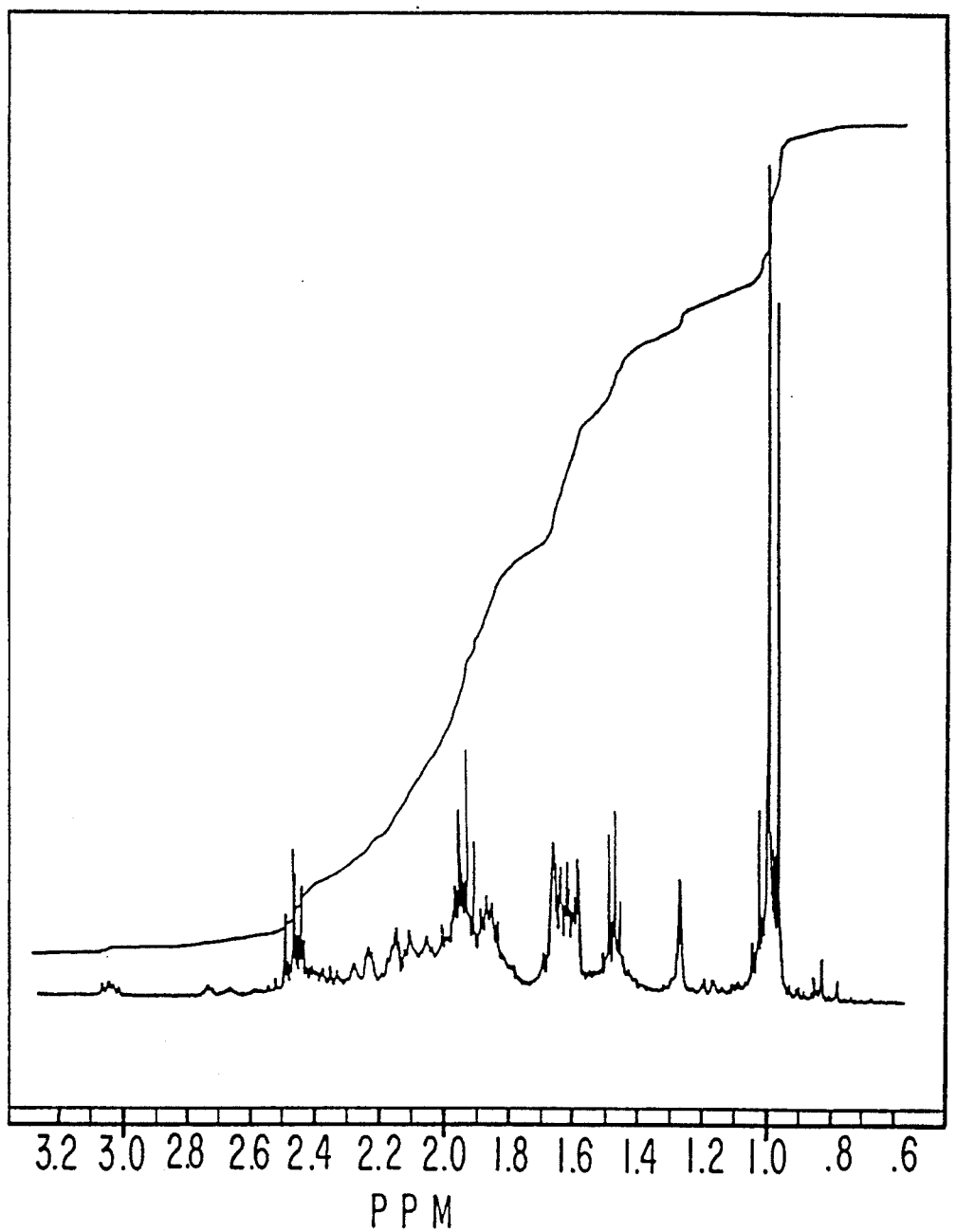
FIG.1-D

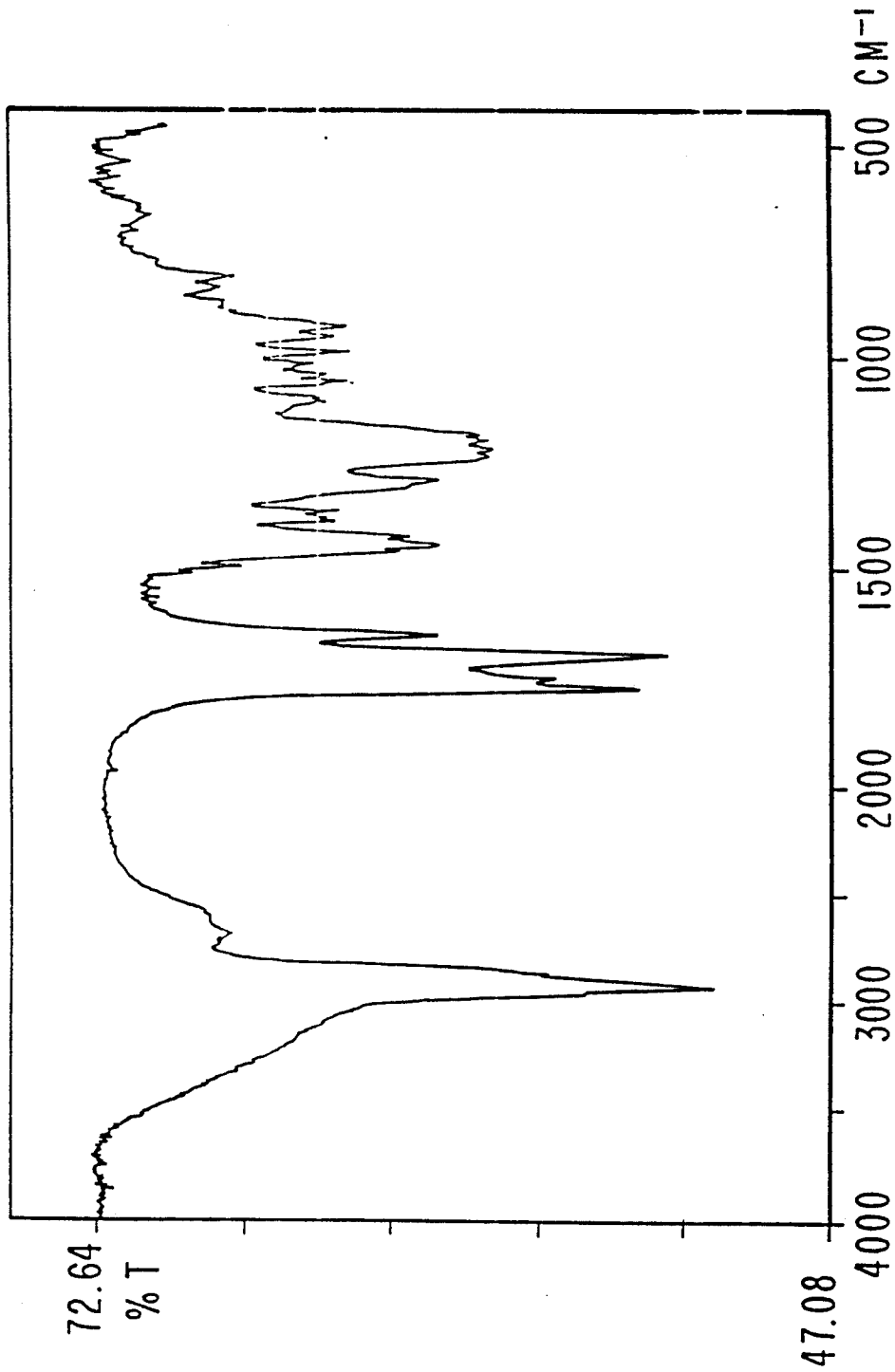

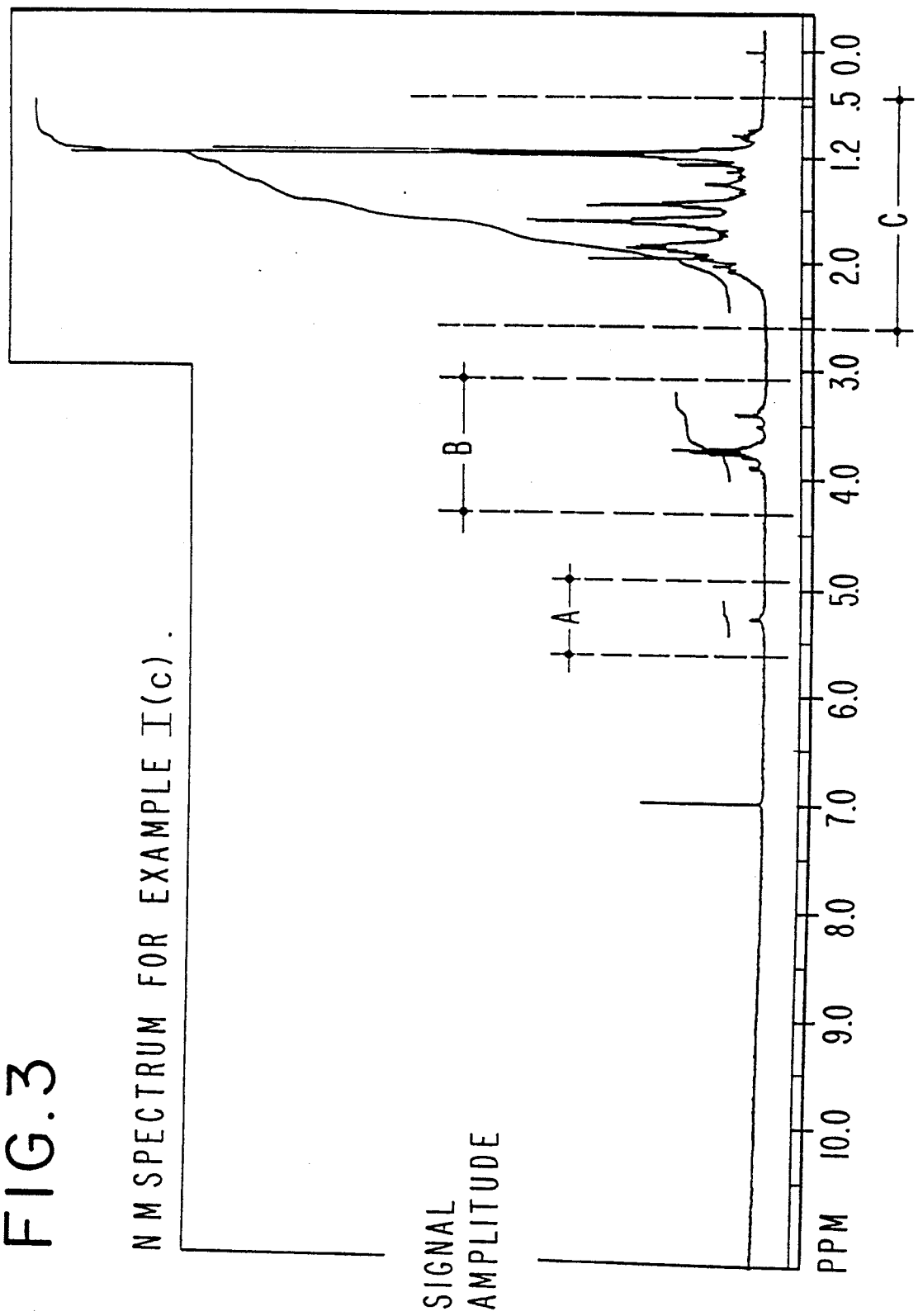

FIG.3-A 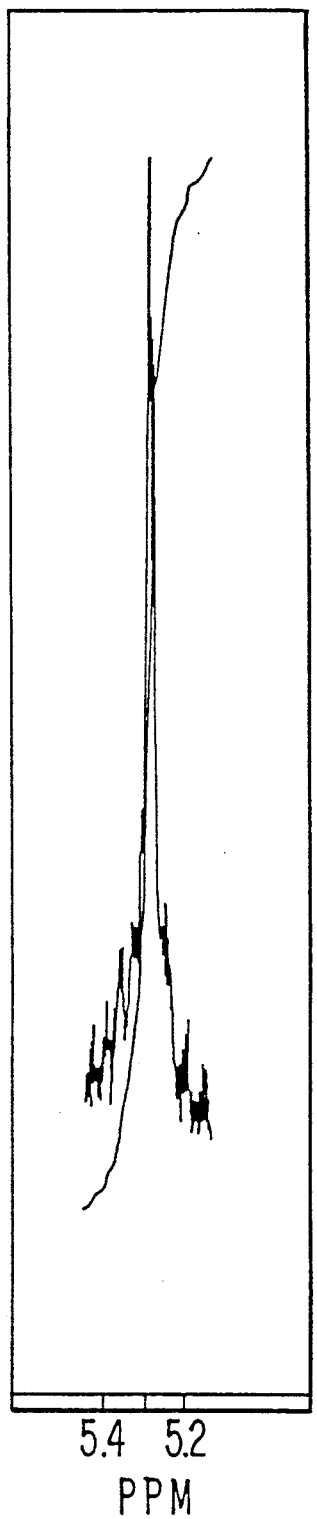
FIG.3-B 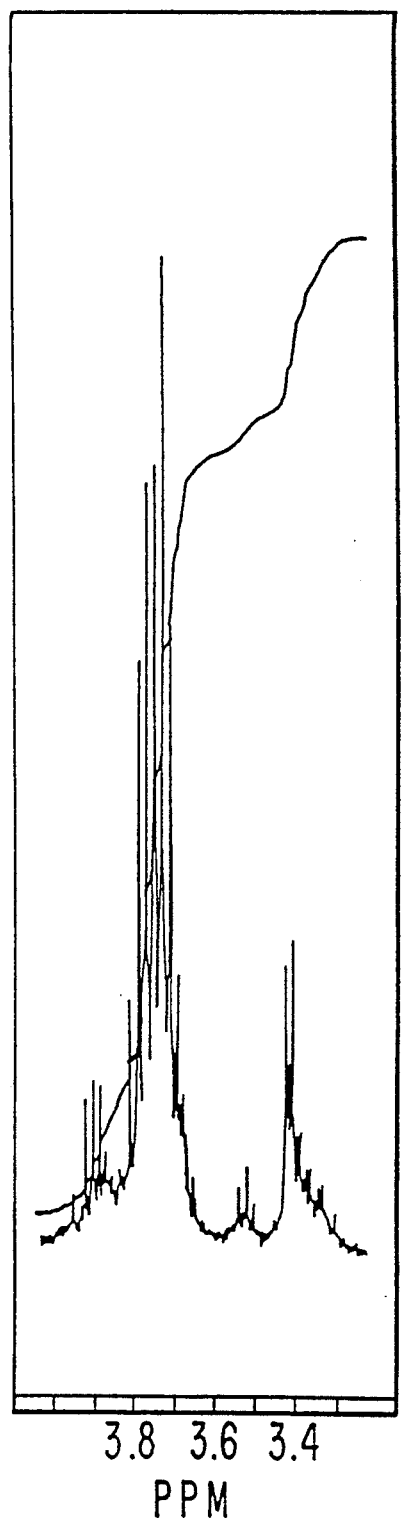

FIG.3-C
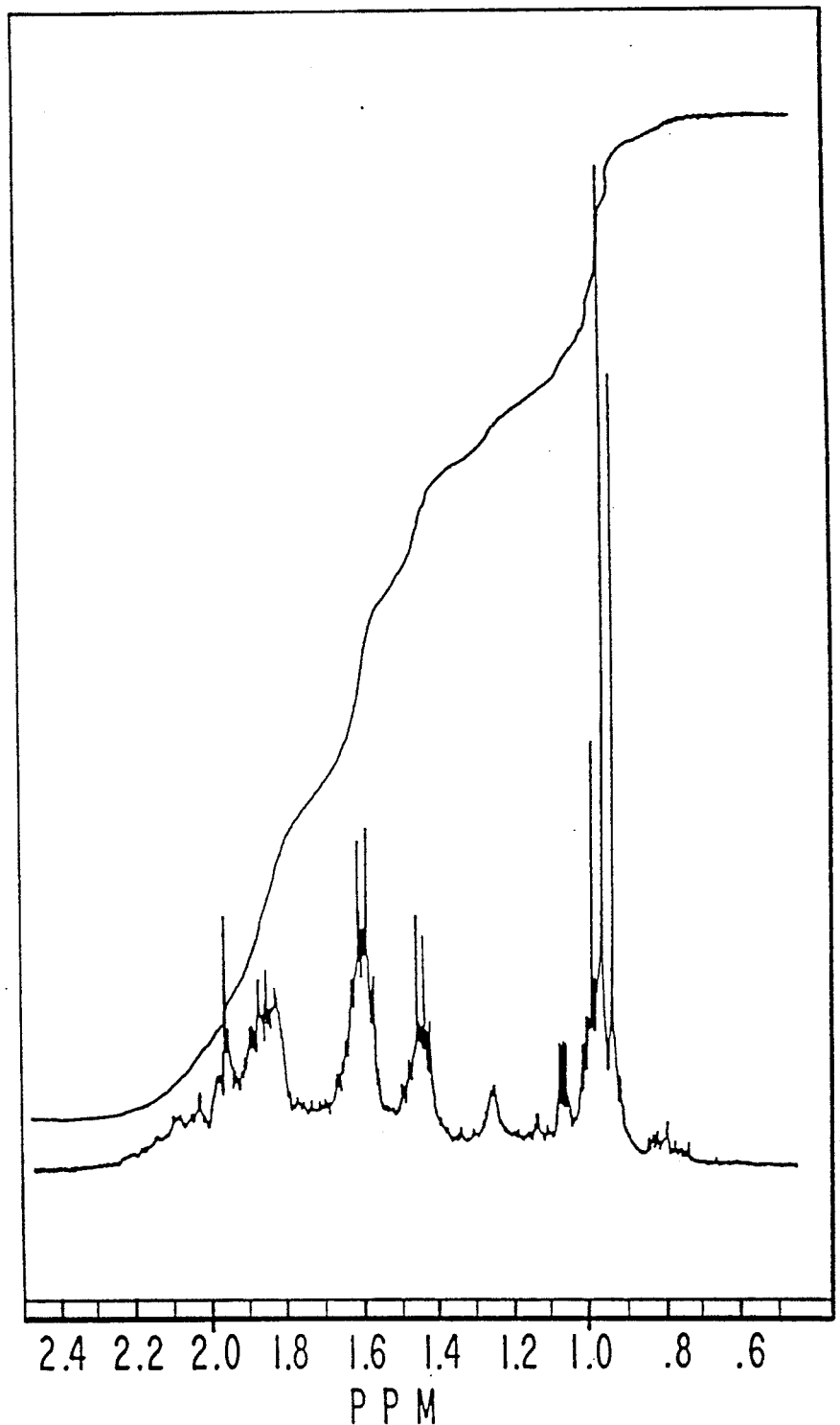

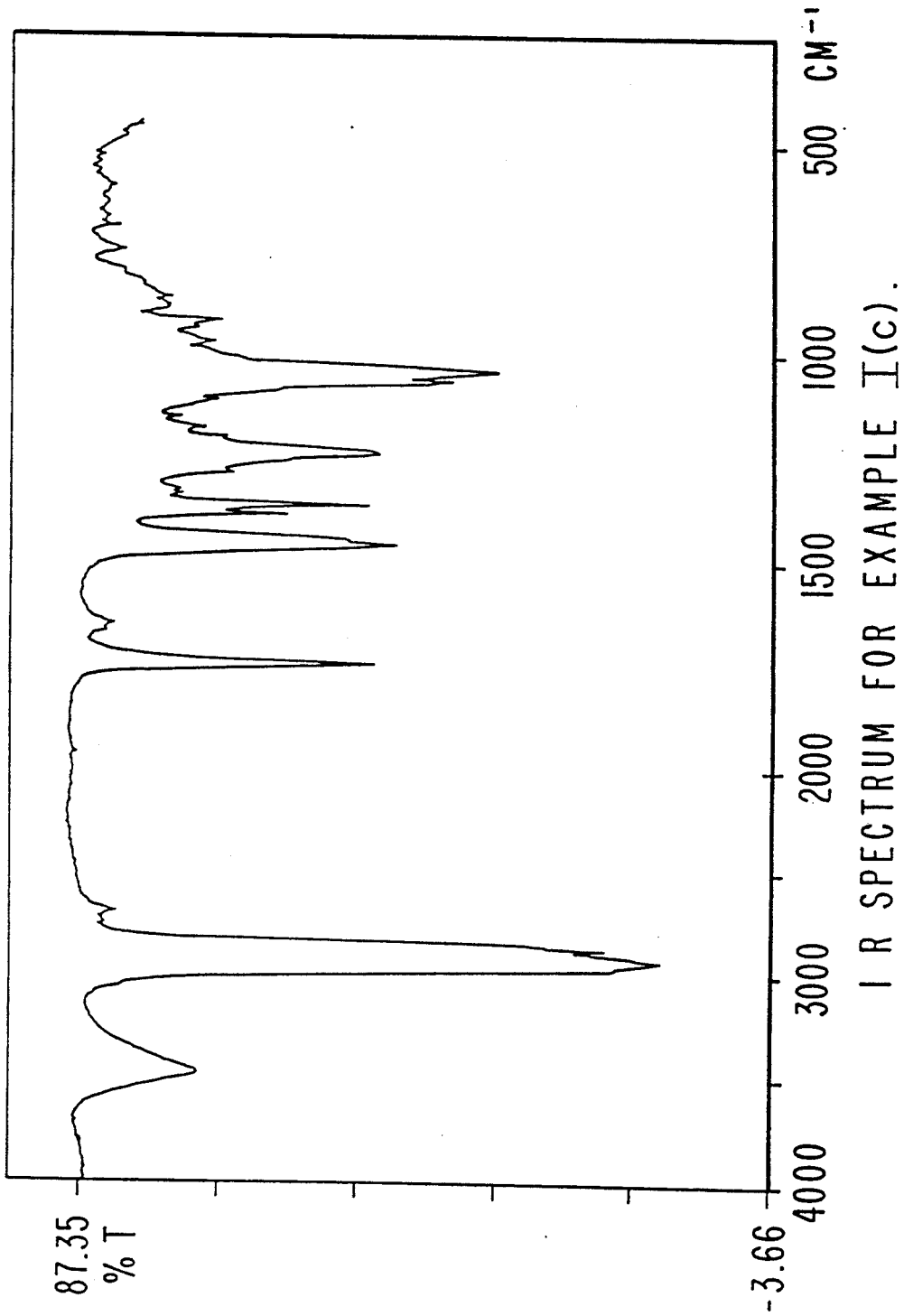

NMR SPECTRUM FOR EXAMPLE III.

FIG.5-A
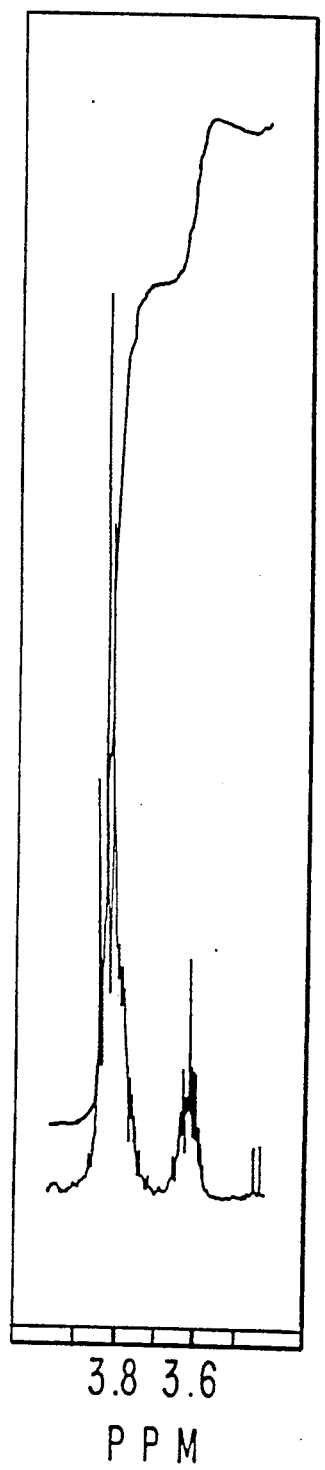

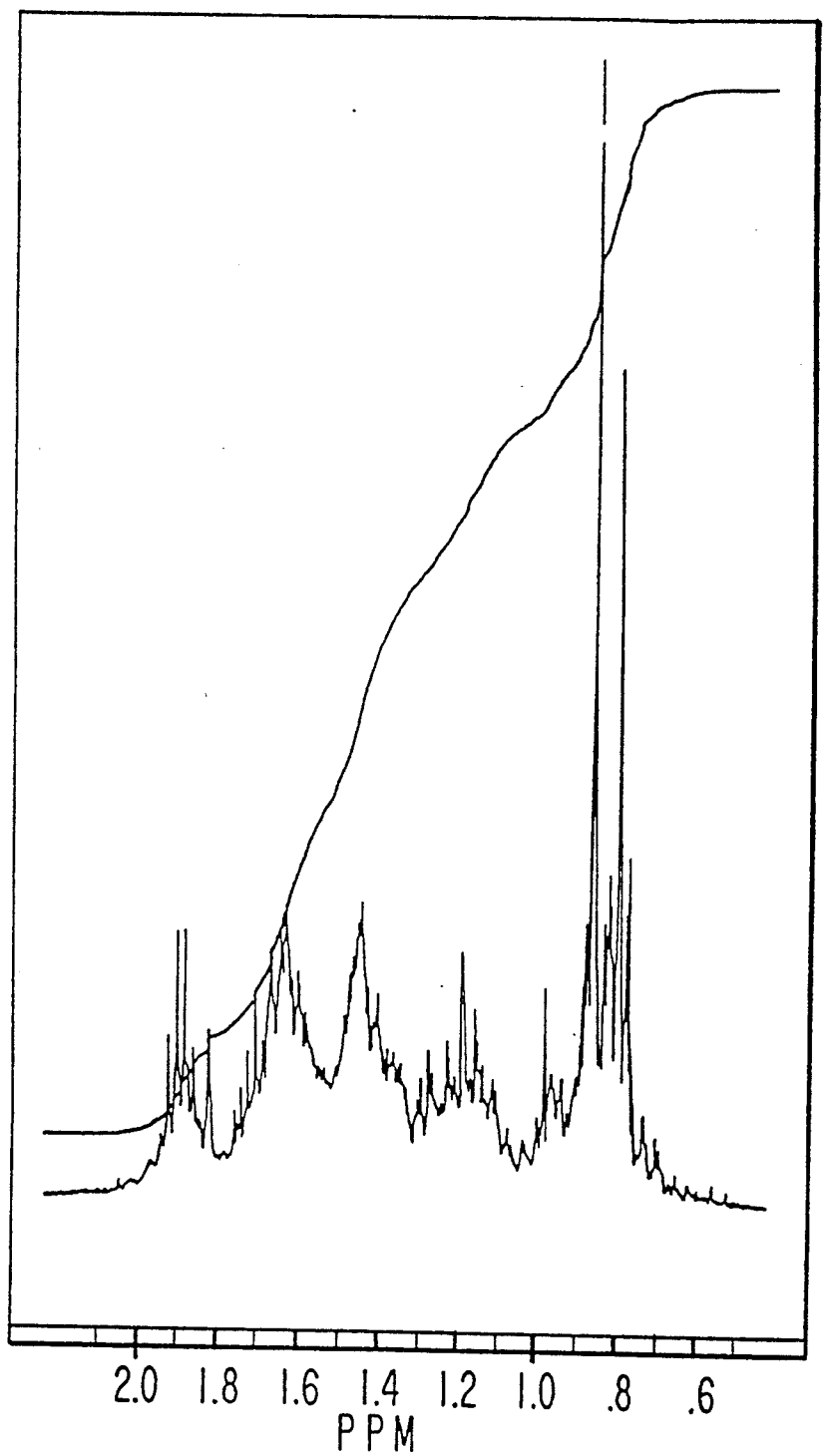
FIG.5-B

IR SPECTRUM FOR EXAMPLE III.

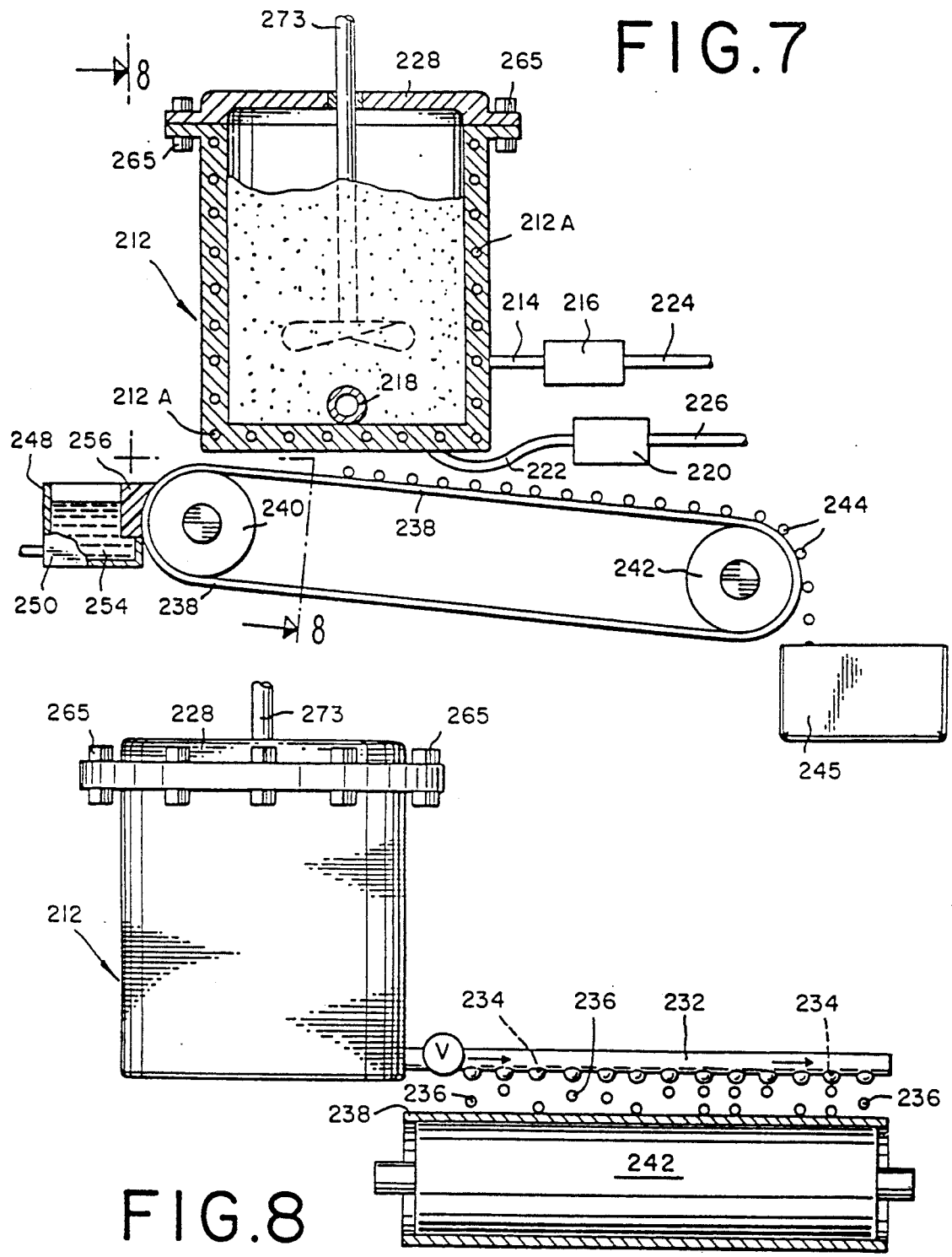

POLYHYDRODIMETHYLNAPHTHALENE SPIROFURAN DERIVATIVES, ORGANOLEPTIC USES THEREOF AND PROCESS FOR PREPARING SAME

This is a divisional of application Ser. No. 965,698, filed Oct. 23, 1992.

BACKGROUND OF THE INVENTION

The instant invention relates to polyhydrodimethylnaphthalene spirofuran derivatives defined according to the structure:

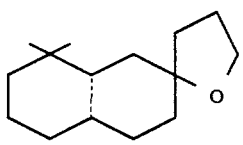

wherein the dashed line represents a carbon-carbon single bond or a carbon-carbon double bond and uses of same in augmenting, enhancing or imparting an aroma of or to perfume compositions, perfumed articles and colognes.

Inexpensive chemical compounds which can provide strong persistent ambergris, ambery, tobacco, woody and animalic aromas, with woody, ambergris, sweet and cigar box-like topnotes are highly desirable in the art of perfumery. Many of the natural materials which provide such fragrances and contribute such desired nuances to perfume compositions as well as perfumed articles are high in cost, unobtainable at times, vary in quality from one batch to another and/or are generally subject to the usual variations of natural products.

There is accordingly, a continuous effort to find synthetic materials which will replace, enhance or augment the fragrance notes provided by natural essential oils or compositions thereof. Unfortunately, many of the synthetic materials either have the desired nuances only to a relatively small degree or they contribute undesirable or unwanted odor to the compositions.

Of particular importance are odorants of the amber type in perfumery.

Enninga, et al, U.S. Pat. No. 3,045,028 issued on Jul. 17, 1962 discloses a number of polymethyl polyhydronaphthofurans, with some of such materials having an amber aroma and others having no amber aroma. Thus, Enninga, et al states that the compound having the structure:

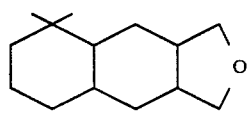

has no amber character but has an odor of the woody type. Enninga, et al further states that the compounds having the structures:

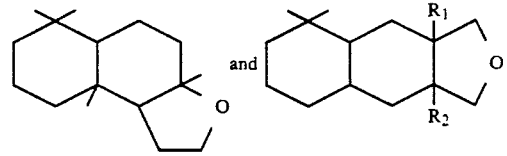

do have amber aromas wherein, in the compound having the structure:

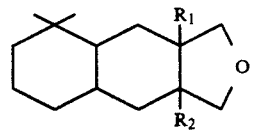

$R_1$ and $R_2$ each represent methyl or hydrogen with at least one of $R_1$ and $R_2$ being methyl. Enninga, et al further discloses the compounds having the structures:

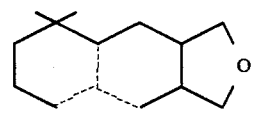

(where one of the dashed lines represents a carbon-carbon double bond and each of the other of the dashed lines represent carbon-carbon single bonds) as an intermediate in preparing perfumery compounds. By means of a process closely similar to that of Enninga, et al, Chodroff in U.S. Pat. No. 3,417,107 discloses the preparation of the compounds having the structures:

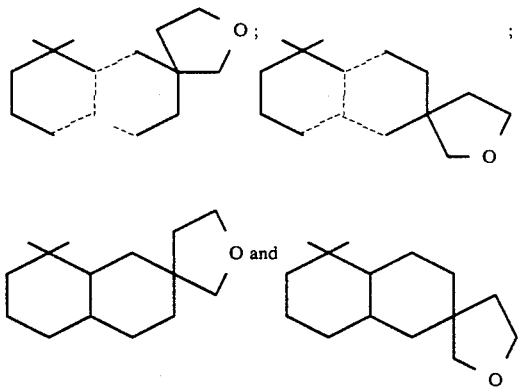

wherein, one of the dashed lines represents a carbon-carbon double bond and each of the other of the dashed lines in each of the compounds represent carbon-carbon single bonds.

Chodroff, et al in U.S. Pat. No. 3,417,107 discloses that such compounds have ambergris-type aromas and also states that such compounds have high degrees of persistence. Nevertheless, compounds having high substantivity, and relatively high strengths in the ambergris area are lacking in commerce.

The compounds of our invention defined according to the generic structure:

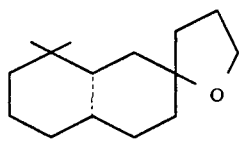

which covers the two compounds, to wit:

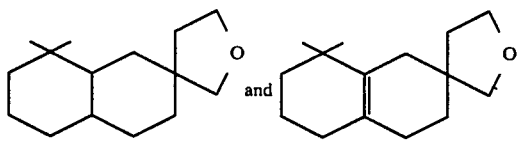

have degrees of persistence approximately three-fold that of the compounds of the prior art and have strengths approximately three-fold that of the prior art (in the ambergris area). Thus, the compounds of our invention, the polyhydrodimethylnaphthalene spirofuran derivatives of our invention, have unexpected, unobvious and advantageous utilities when compared with compounds having similar structures in the prior art.

Indeed, other compounds of the prior art have vastly different aromas from the polyhydrodimethylnaphthalene spirofuran derivatives of our invention, to wit:
the compound having the structure:

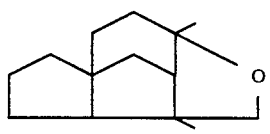

of Blumenthal, et al, U.S. Pat. No. 3,281,432; and the compounds of Sprecker, et al having the structure:

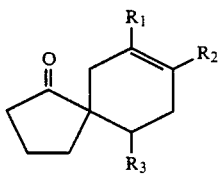

of U.S. Pat. No. 4,639,330 wherein, one of $R_1$ or $R_2$ is hydrogen and the other of $R_1$ or $R_2$ is methyl and wherein, $R_3$ represents $C_3$–$C_4$ alkyl.

Our invention also relates to intermediates useful in preparing the polyhydrodimethylnaphthalene spirofuran derivatives of our invention, defined according to the structures:

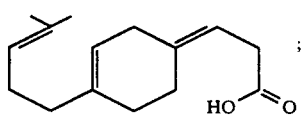

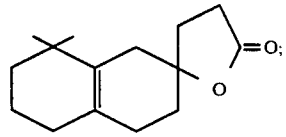

and

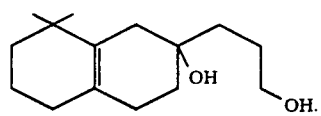

A compound similar to the compound having the structure:

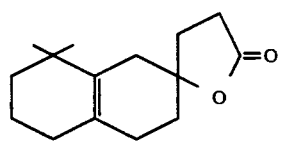

is disclosed by Jacobson, Tetrahedron Letters, Vol. 21(13), pages 1205–1208 (1980) in a paper entitled "Three Carbon Annelation Reagents: Unsaturated Alpha Aminonitriles As Homoenolate Equivalents". Jacobson discloses the compound having the structure:

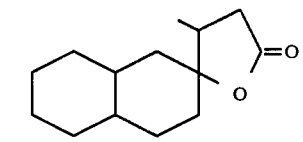

which is somewhat related to the intermediate of our invention having the structure:

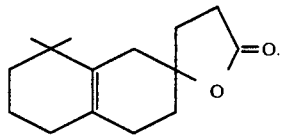

Furthermore, other spironaphthalene derivatives are known in the prior art but their structures and properties are totally distinct from the structures and properties of the polyhydrodimethylnaphthalene spirofuran derivatives of our invention. Thus, Hall, et al, U.S. Pat. No. 4,010,286 discloses the organoleptic utilites of the compounds having the structures:

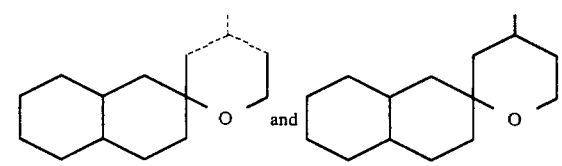

wherein, one of the dashed lines in the mixture of compounds defined according to the structure:

is a carbon-carbon double bond and each of the other of the dashed lines represent carbon-carbon single bonds.

BRIEF DESCRIPTION OF THE DRAWINGS

FIG. 1 is the NMR spectrum for the reaction product of Example I(a) containing the compounds having the structures:

FIGS. 1A, 1B, 1C and 1D are enlargements of sections "A", "B", "C" and "D" of the NMR spectrum of FIG. 1.

FIG. 2 is the infra-red spectrum for the reaction product of Example I(a) containing the compounds having the structures:

FIG. 3 is the NMR spectrum for the reaction product of Example I(c) containing the compound having the structure:

FIGS. 3A, 3B and 3C are enlargements of sections "A", "B" and "C" of the NMR spectrum of FIG. 3.

FIG. 4 is the infra-red spectrum of the reaction product of Example I(c) containing the compound having the structure:

produced according to Example III.

Figure 5:
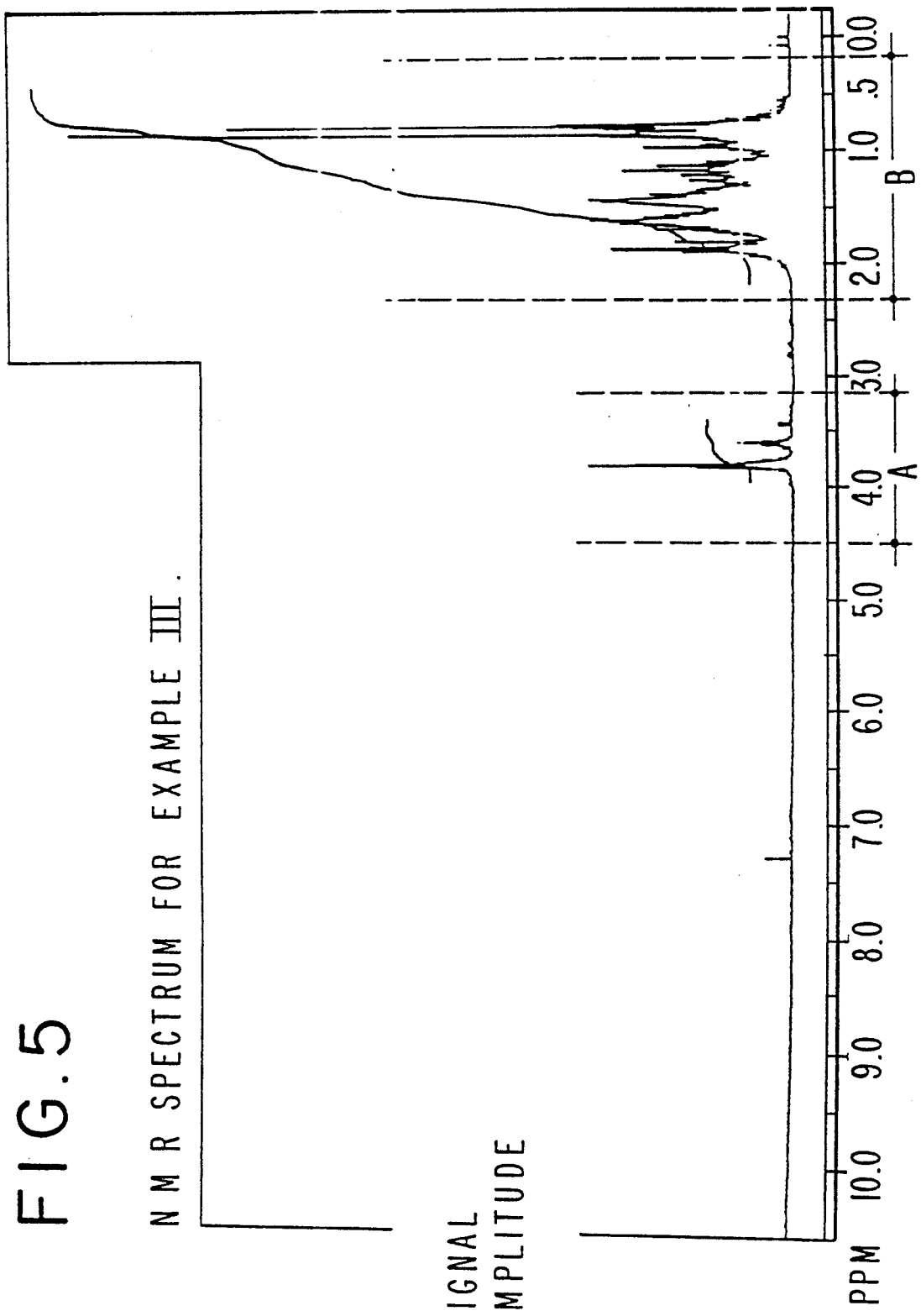
FIG. 5 is the NMR spectrum for the compound having the structure.

FIGS. 5A and 5B are enlargements of sections "A" and "B" of the NMR spectrum of FIG. 5.

Figure 6:
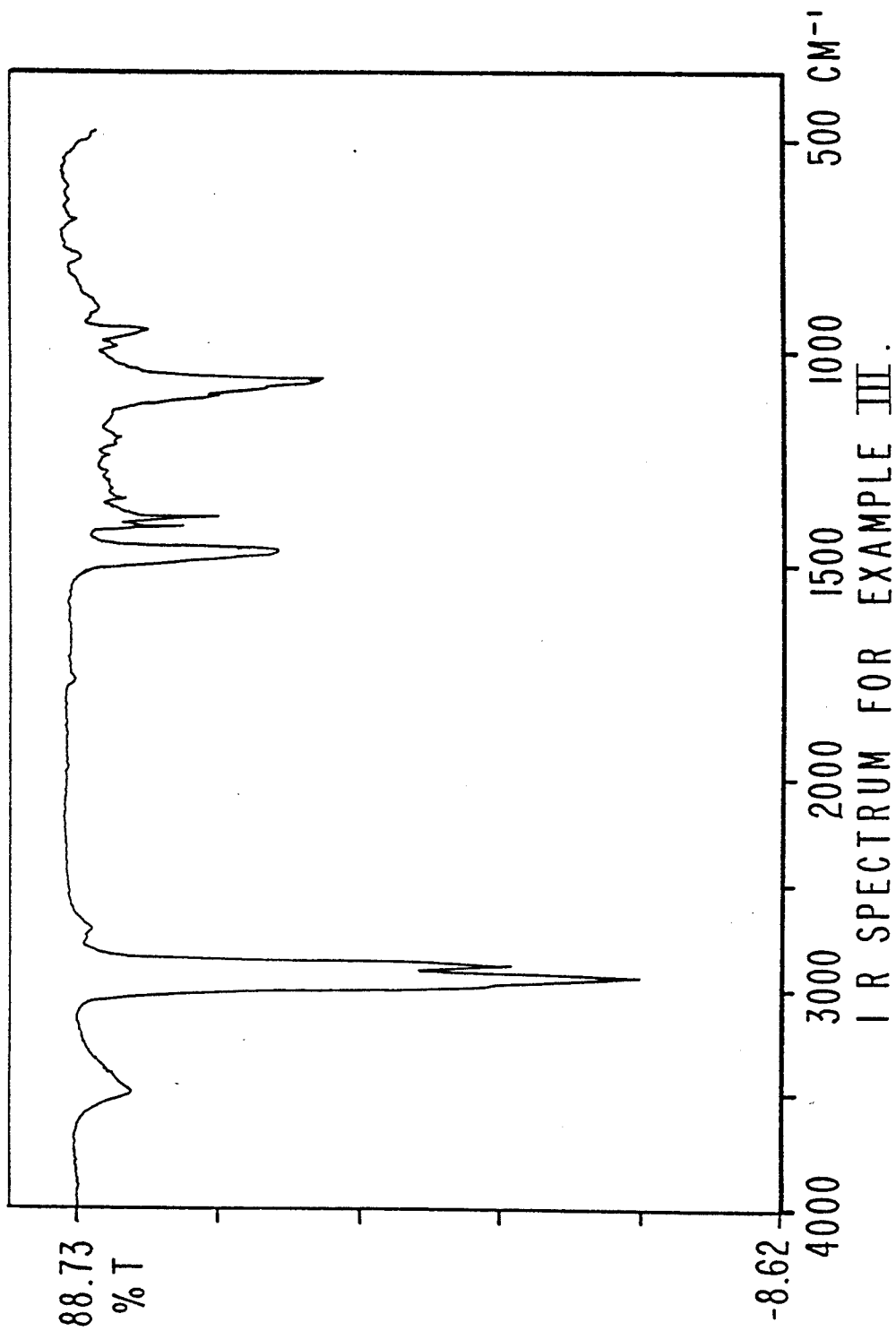

FIG. 6 is the IR spectrum for the compound having the structure:

prepared according to Example III.

FIG. 7 is a partial side elevation view and partial sectional view of an apparatus for forming polymer pellets containing at least one of the polyhydrodimethylnaphthalene spirofuran derivatives of our invention.

FIG. 8 is a section taken along line 8—8 of FIG. 7.

DETAILED DESCRIPTION OF THE DRAWINGS

Referring to FIGS. 7 and 8, the apparatus used in producing polymeric fragrances containing one or more of the polyhydrodimethylnaphthalene spirofuran derivatives of our invention comprises a device for forming scented polyolefin for example) pellets, which comprises a vat or container 212 into which a mixture of polyolefin such as polyethylene and an aromatic substance or scented material is placed (in this case at least one of the polyhydrodimethylnaphthalene spirofuran derivatives of our invention).

The container is closed by an air-tight lid 228 and the air-tight lid 228 is clamped to the container 212 by bolts 265.

A stirrer 273 traverses the lid or cover 228 in an air-tight manner and is rotated in a suitable manner.

Container 212 having heating coils 212A which are supplied with electric current through cable 224 from a rheostat or control 216 is operated to maintain a temperature inside the container 212 such that polyethylene or other theromplastic polymer in the container will be maintained in the molten or liquid state. It has been found advantageous to employ a colorless, odorless polymer (e.g., polyethylene) with viscosity ranging between 180 and 220 saybolt seconds and having a melting point in the range of 200°–280° F. The heater 212A is operated to maintain the upper portion of the container 212 within a temperature range of from 250°–350° F. The bottom portion of the container is heated by means of heating coils 212A heated through control 220 connected thereto through a connecting wire 222 to maintain the lower portion of the container within a temperature range of from 250°-350° F.

Thus, polymer (e.g., polyethylene) is added to container 212 and is heated from 10-12 hours whereafter a scented aroma imparting material (at least one of the polyhydrodimethylnaphthalene spirofuran derivatives of our invention) is added quickly to the melt. The material must be compatible with the polyolefin and forms a homogeneous liquid melt therewith. The scented material is of a type for the particular aroma desired and formulated specifically for the scenting purpose for which the polyolefin will be employed.

Generally, about 5-30% by weight of the scented material (containing at least one of the polyhydrodimethylnaphthalene spirofuran derivatives of our invention) are added to the polyolefin.

After the scent imparting material (e.g., a composition containing at least one of the polyhydrodimethylnaphthalene spirofuran derivatives of our invention) is added to the container 212, the mixture is stirred for a few minutes, for example, 5-15 minutes, and maintained within the temperature range as indicated, supra, by means of heating coils 212A.

The controls 216 and 220 are connected, respectively, through cables 214 and 222, respectively, to heating coils 212A. The said controls 216 and 220 are also connected through cables 224 and 226, respectively, to a suitable power supply of electric current for supplying the electric power to the heating coils 212A for heating purposes.

Thereafter the valve "V" is opened permitting the mass to flow outwardly through conduit 218/232 having a multiplicity of orifices 234, adjacent to the lower side thereof. The outer end of the conduit 218/232 is closed so that the liquid polymer (e.g., polyolefin) and aroma imparting material (e.g., at least one of the polyhydrodimethylnaphthalene spirofuran derivatives of our invention) will continuously drop through orifices 234 downwardly from conduit 232. During this time the temperature of the polymer (e.g., polyolefin) and scent imparting material (e.g., a mixture containing at least one of the polyhydrodimethylnaphthalene dimethylnaphthalene spirofuran derivatives of our invention) is accurately controlled so that a temperature in the range of from about 210°-275° F. will exist in the conduit 218/232. The regulation of the temperature through the controls 216 and 220 is essential in order to insure temperature balance to provide for the continuous dropping or dripping of molten polymer (e.g., polyethylene) and scenting material (e.g., one or more of the polyhydrodimethylnaphthalene spirofuran derivatives of our invention) mixture through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238 they form pellets 244 which harden almost instantaneously and fall off the end of the conveyor 238 into a container 245 and utilized in processes as illustrated, infra.

A feature of this aspect of the process of our invention is the provision for moistening the conveyor belt 238 to insure rapid formation of the solid polymeric (e.g., polyolefin) scented pellets 244 without sticking to the belt. The belt 238 is advantageously fabricated of a material which will not normally stick to a melted plastic but a moistening means 248 insures a sufficiently cold temperature of the belt surface for an adequate formation of the pellets 244. The adequate moistening means comprises a container 250 which is continuously fed with water 254 to maintain a level for moistening a sponge element 256 which bears against the exterior of the belt 238.

THE INVENTION

The present invention provides polyhydrodimethylnaphthalene spirofuran derivatives defined according to the generic structure:

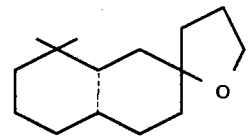

wherein, the dashed line represents a carbon-carbon single bond or a carbon-carbon double bond and intermediates for producing such polyhydrodimethylnaphthalene spirofuran derivatives defined according to the structures:

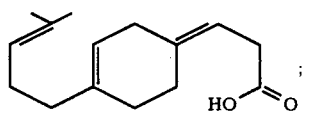

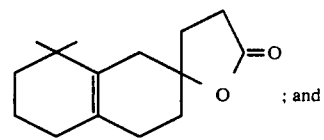

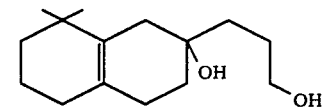

as well as processes for preparing such polyhydrodimethylnaphthalene spirofuran derivatives.

The compositions of matter of our invention produced according to the processes of our invention are capable of augmenting, enhancing or providing strong, persistent, ambergris, ambery, tobacco, woody and animalic aromas, with woody, ambergris, sweet and cigar box-like topnotes to perfume compositions, colognes and perfumed articles (e.g., solid or liquid, anionic, cationic, nonionic or zwitterionic detergents, fabric softener articles, drier-added fabric softener articles, fabric softener compositions, cosmetic powders, hair preparations, perfumed polymers and the like).

The substances of our invention are prepared by means of first reacting the aldehyde defined according to the structure:

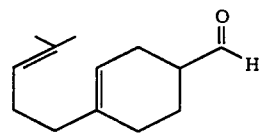

with malonic acid having the structure:

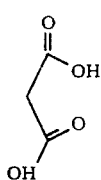

according to the reaction:

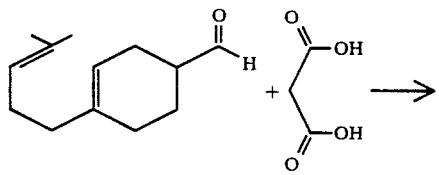

to prepare a mixture of compounds having the structures:

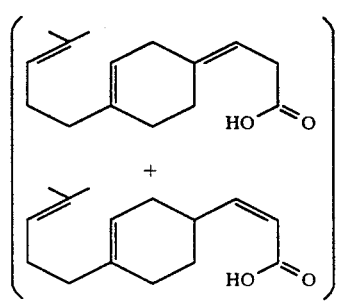

Only the compound having the structure:

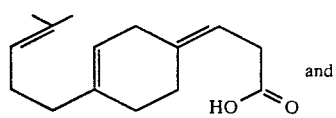

can be further cyclized to ultimately yield the final product desired in our composition of matter. The compound having the structure:

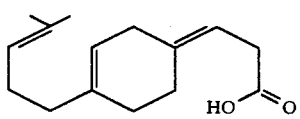

will not give rise ultimately to the compounds defined according to the structure:

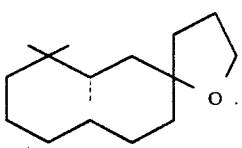

The compound having the structure:

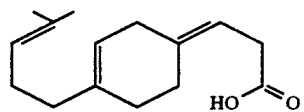

is then cyclized according to the reaction:

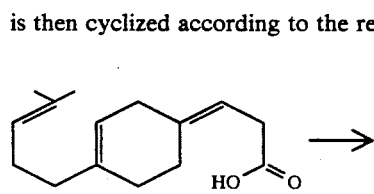

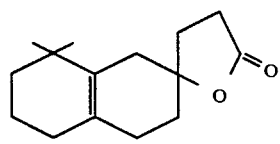

The resulting compound defined according to the structure:

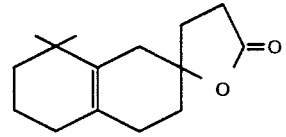

is a novel compound.

The compound having the structure:

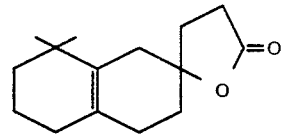

is then reduced according to the reaction:

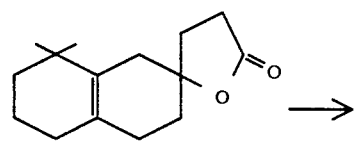

in order to yield the novel compound of our invention having the structure:

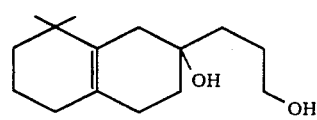

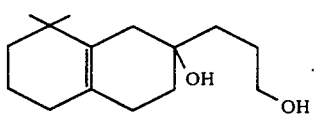

The compound having the structure:

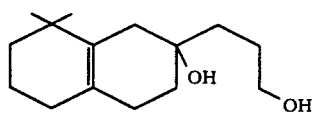

is then recyclized according to the reaction:

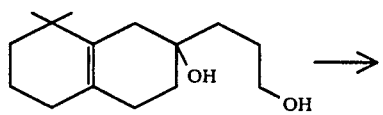

in order to yield the compound having the structure:

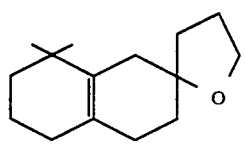

This compound is used "as is" is perfumery or it may be distilled and further reduced by means of hydrogen using a hydrogenation catalyst to form the compound having the structure:

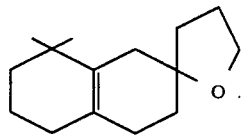

according to the reaction:

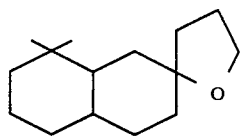

More specifically, the reaction, to wit:

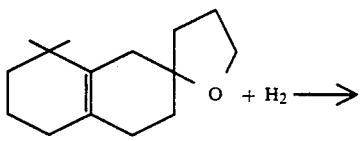

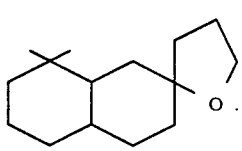

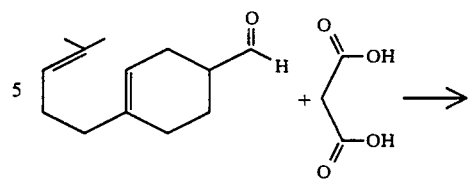

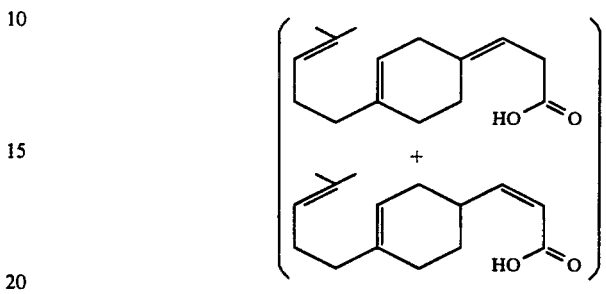

takes place in the presence of triethylamine at a temperature of between about 80° and 90° C. for a period of time of between about two and about five hours or at higher temperatures in the absence of said triethylamine.

The product having the structure:

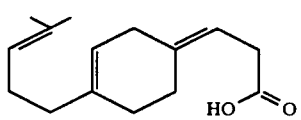

is then distilled from the mixture of compounds having the structures:

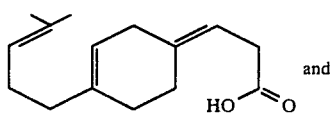

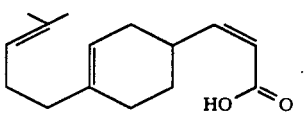

The resulting product is then cyclized according to the reaction:

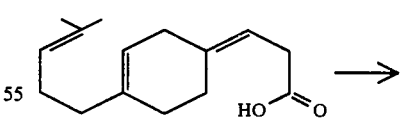

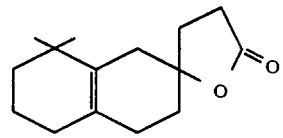

in the presence of a cyclization reagent, preferably methane sulphonic acid or phosphoric acid at a temperature of from about 100° C. up to about 110° C. for a period of time of between about four and about ten hours.

The resulting product having the structure:

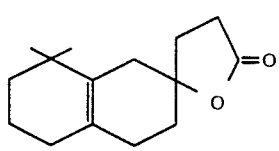

is then fractionally distilled and is reduced using a reducing agent such as VITRIDE® having the structure:

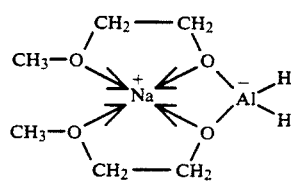

or lithium aluminum hydride (LiAlH₄) according to the reaction:

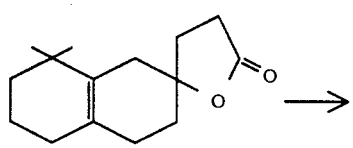

to produce the compound having the structure:

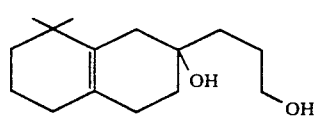

a novel compound. This compound is then recyclized according to the reaction:

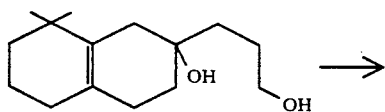

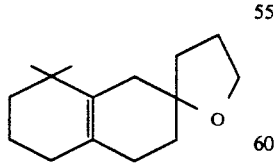

using a strong cyclizing agent, e.g., KHSO₄ or p-toluene sulphonic chloride at a temperature of between about 80° and 160° C. for a period of time of between about one and seven hours. At the end of the reaction the reaction mass is fractionally distilled to yield the product having the structure:

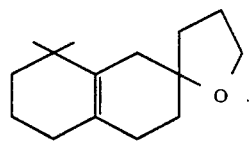

The resulting compound having the structure:

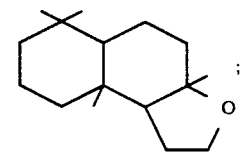

has a strong, persistent, ambergris aroma, with ambergris topnotes. On a scale of 1-10 its persistence and strength are both "10" as compared to the prior art compounds having the structures:

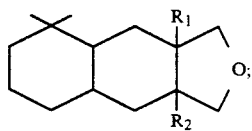

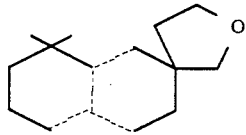

(wherein, R₁ and R₂ are hydrogen or methyl with at least one of R₁ or R₂ being methyl) and

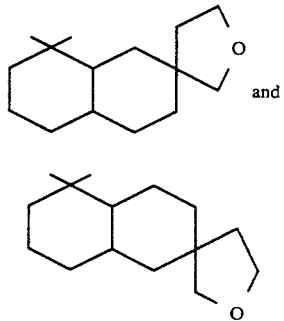

wherein, one of the dashed lines in each of the compounds having the dashed lines is a carbon-carbon double bond and the other of the dashed lines represent carbon-carbon single bonds) which each have a strength and persistence of between 2 and 4 (on a scale of 1-10).

The resulting compound having the structure:

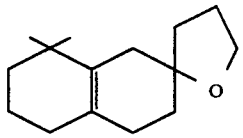

may then be hydrogenated according to the reaction:

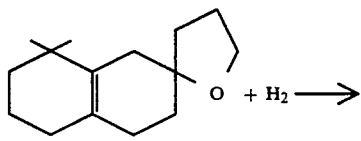

using a hydrogenation catalyst to yield the compound having the structure:

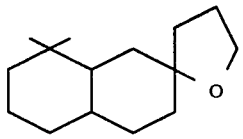

An example of an useful hydrogenation catalyst is palladium/aluminum with hydrogenation conditions at about 150°-200° C. and from about 300-1000 psig for a period of time of from about ten up to about twenty hours. The reaction mass is filtered and fractionally distilled yielding substantially pure compound having the structure:

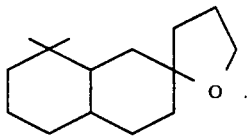

which has a strong, persistent, ambery, tobacco, woody and animalic aroma, with woody, sweet and cigar box-like topnotes.

Accordingly, the following table sets forth the perfumery properties of the polyhydrodimethylnaphthalene spirofuran derivatives of our invention:

TABLE I

| Structure of Compound | Perfumery Property |
| --- | --- |
| The compound having the structure: | A strong, persistent, ambergris aroma, with ambergris topnotes. |

TABLE I-continued

| Structure of Compound | Perfumery Property |
| --- | --- |
| 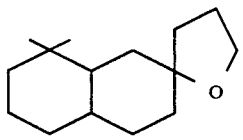 prepared according to Example II, bulked distillation fractions 6-11. The compound having the structure: [structure] prepared according to Example III, bulked distillation fractions 6-8. | A strong, persistent, ambery, tobacco, woody and animalic aroma, with woody, sweet and cigar box-like topnotes. |

One or more of the polyhydrodimethylnaphthalene spirofuran derivatives of our invention prepared in accordance with the process of our invention and one or more auxiliary perfume ingredients including, for example, alcohols, aldehydes, ketones, terpenic hydrocarbons, nitriles, esters, lactones, ethers other than the ethers of our invention, natural essential oils and synthetic essential oils may be admixed so that the combined odors of the individual components produce a pleasant and desired fragrance, particularly and preferably in the amber fragrances Such compositions usually contain:

(a) the main note or the "bouquet" or foundation stone of the composition;

(b) modifiers which round-off and accompany the main note;

(c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute their particular olfactory characteristics, however, the overall sensory effect of the perfume composition will be at least the sum total of the effects of each of the ingredients. Thus, the polyhydrodimethylnaphthalene spirofuran derivatives prepared in accordance with the processes of our invention can be used to alter, modify or enhance the aroma characteristic of a perfume composition, for example, by utilizing or moderating the olfactory reaction contributed by another ingredient in the composition.

The amount of the polyhydrodimethylnaphthalene spirofuran derivatives prepared in accordance with the processes of our invention which will be effective in perfume compositions as well as in perfumed articles (e.g., anionic, cationic, nonionic or zwitterionic detergents, soaps, fabric softener compositions, fabric softener articles and perfumed polymers) and colognes depends upon many factors including the other ingredients, their amounts and the effects which are desired. It has been found that perfume compositions containing as little as 0.01% of the polyhydrodimethylnaphthalene spirofuran derivatives prepared in accordance with the processes of our invention or even less (e.g., 0.005%) can be used to impart, augment or enhance strong, persistent, ambergris, ambery, tobacco, woody and animalic aroma nuances, with woody, ambergris, sweet and cigar box-like topnotes to soaps, cosmetics, anionic, cationic, nonionic or zwitterionic detergents, fabric softener articles, microporous polymers, particularly acrylic resins, polyethylenes and other products. The amount employed can range up to 70% of the fragrance components and will depend on considerations of cost, nature of the end product, the effect desired on the finished product and the particular fragrance sought.

The polyhydrodimethylnaphthalene spirofuran derivatives of our invention prepared in accordance with the processes of our invention are useful (taken alone or together with other ingredients in perfume compositions) as (an) olfactory component(s) in detergents and soaps, space odorants and deodorants, perfumes, colognes, toilet water, bath preparations such as creams, deodorants, hand lotions, and sun screens; powders, such as talcs, dusting powders, face powders, microporous "perfumed" slow release polymers and the like.

When used as (an) olfactory component(s) in perfumed articles, as little as 0.005% of the polyhydrodimethylnaphthalene spirofuran derivatives of our invention prepared in accordance with the processes of our invention will suffice to impart, augment or enhance strong, persistent, ambergris, ambery, tobacco, woody and animalic aroma nuances, with woody, ambergris, sweet and cigar box-like topnotes. Generally, no more than 6% of the polyhydrodimethylnaphthalene spirofuran derivatives of our invention based on the ultimate end product is required in the perfumed article. Accordingly, the range of use of the polyhydrodimethylnaphthalene spirofuran derivatives of our invention in perfumed articles, per se, is from about 0.005% up to about 6% by weight based on the perfumed article.

In addition, the perfume composition or fragrance composition of our invention can contain a vehicle or carrier for one or more of the polyhydrodimethylnaphthalene spirofuran derivatives of our invention. The vehicle can be a liquid such as a non-toxic alcohol, e.g., ethyl alcohol, a non-toxic glycol, e.g., propylene glycol or the like. The carrier can be an an absorbent solid such as a gum (e.g., gum arabic, guar gum or xanthan gum or combinations thereof) or components for encapsulating the composition (such as by coacervation) or using prepolymers such as urea-formaldehyde prepolymers which are able to form a urea-formaldehyde polymer capsule around a liquid perfume center.

It will thus be apparent that the polyhydrodimethylnaphthalene spirofuran derivatives of our invention can be utilized to alter, modify or enhance sensory properties particularly organoleptic properties such as fragrances of a wide variety of consumable materials.

The following Examples I, II and III set forth means for preparing the polyhydrodimethylnaphthalene spirofuran derivatives of our invention. The examples including and following Example IV, infra, set forth illustrations of organoleptic utilites of the polyhydrodimethylnaphthalene spirofuran derivatives of our invention.

All parts and percentages given herein are by weight unless otherwise specified.

EXAMPLE I

Preparation of 3',4,4',5,5',6',7',8'-Octahydro-8',8'-Dimethyl Spiro[Furan-2(3H), 2'(1'H)-Naphthalene]

Example I(a)

Knoevenagel Condensation

Reaction:

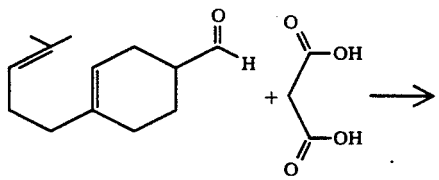

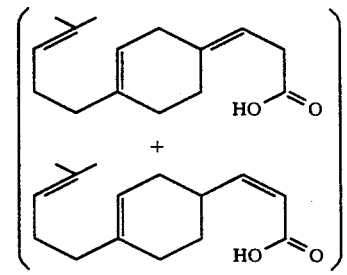

Into a 2 liter reaction vessel are placed 500 grams triethyl amine; 240 grams malonic acid and 384 grams of myrac aldehyde having the structure:

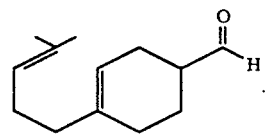

With stirring, the reaction mass is slowly heated to 85° C. Gas evolution starts at a temperature of 75° C. The reaction mass is stirred for a period of five hours after which an additional 50 grams of malonic acid is added. The reaction mass is continued to be stirred for an additional seven hours.

Triethyl amine is then stripped off from the reaction mass until the reaction mass temperature reaches 110° C. The reaction mass is then cooled to room temperature.

500 Grams of toluene is then added to the reaction mass with stirring. 250 Grams of concentrated hydrochloric acid followed by 250 grams of water is then added to the reaction mass.

The reaction mass is then stirred for a period of 0.5 hours; and the reaction mass now exists in two phases; an organic phase and an aqueous phase. The organic phase is washed with two 250 gram volumes of water. 40 Grams of phosphoric acid is then added to the washed organic phase and the washed organic phase is stirred for a period of five hours at a temperature of 70° C.

Cyclization Using Methane Sulphonic Acid

Reaction:

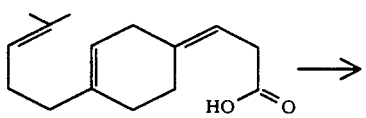

→

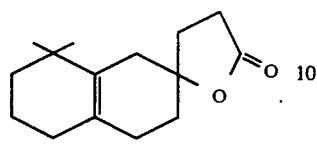

5 Grams of methane sulphonic acid is added to the reaction mass and the reaction mass is heated to 100° C. and maintained at 100° C. for a period of five hours. IR and NMR analyses indicate that cylization has occurred and the ratio of lactone having the structure:

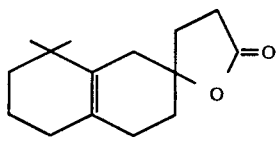

to carboxylic acid having the structure:

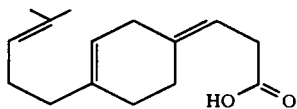

is 4:1.

The reaction mass is washed with 100 grams of 5% aqueous sodium carbonate followed by 100 grams of water. The reaction mass is stripped and distilled yielding 274 grams of distillate having the structure:

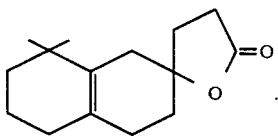

FIGS. 1 and 2, supra, indicate the NMR and IR analyses, respectively.

EXAMPLE I(b)

Reduction of Lactone with Lithium Aluminum Hydride

Reaction:

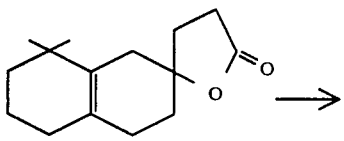

→

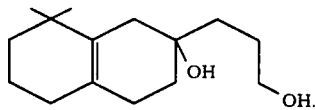

Into a 2 liter reaction vessel is placed 274 grams of the compound having the structure:

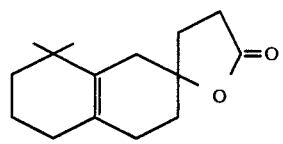

prepared according to Example I(a) and 400 ml of one molar lithium aluminum hydride in tetrahydrofuran.

The reaction mass is then heated to reflux (66° C.) and refluxed for a period of three hours.

75 Grams of ethyl acetate in 50 grams of tetrahydrofuran is added to the reaction mass over a period of one hour. The reaction mass is then refluxed for an additional one hour. The addition is exothermic.

250 Grams of toluene is added to the reaction mass with stirring. The tetrahydrofuran is then stripped from the reaction mass until the reaction mass temperature is 95° C.

The reaction mass is cooled and 750 grams of 20% acetic acid followed by 500 ml 5% aqueous sodium chloride solution is added thereto.

The reaction mass is stripped at 100° C. and 6 mm/Hg. pressure leaving 132 grams of the crude diol having the structure:

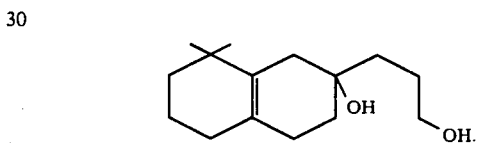

EXAMPLE I(c)

Cyclization of Diol

Reaction:

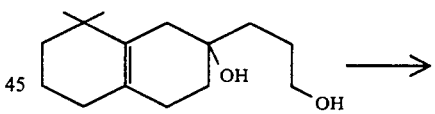

→

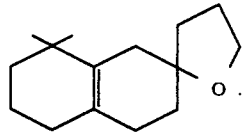

Into a 5 liter reaction vessel is placed 125 grams of the crude diol of Example I(b) having the structure:

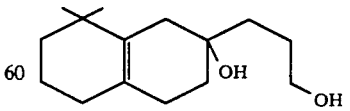

and 350 grams of 95% ethyl alcohol. Over a period of two hours a solution of 705 grams of potassium hydroxide in 2000 grams of water is added to the reaction mass. With stirring, the reaction mass is heated to 56° C. Over a period of one hour, 338 grams of para toluene sulphonic chloride is added to the reaction mass. The reaction mass is then refluxed for a period of four hours at 83° C. Ethyl alcohol is then stripped from the reaction mass until the reaction mass is boiling at 101° C. (vapor temperature).

The reaction mass is diluted with 2 liters of water and extracted with 110 ml of toluene. The toluene extract is then washed with three volumes of water until the pH is 7. The reaction mass is then stripped and distilled yielding 68.6 grams of distillate and 28.7 grams of residue.

A second batch is cyclized using the above conditions with the exception that instead of para toluene sulphonic chloride, 14 grams of potassium acid sulfate (KHSO$_4$) is used as a cyclization reagent at 150° C., 15 mm/Hg. for a period of two hours.

The KHSO$_4$ and para toluene sulphonic chloride cyclization products are combined and distilled through a 10 plate vigreux column yielding the following fractions:

| Fraction No. | Vapor Temp. (°C.) | Liquid Temp. (°C.) | Vacuum mm/Hg. Pressure |
|---|---|---|---|
| 1-3 | 64/103 | 120/144 | 2.4 |
| 4-10 | 103-117 | 142-167 | 2.0 |
| 11-14 | 122-150 | 169-212 | 2.4-0.55. |

The resulting product is analyzed via NMR and GLC (shown in the spectra, supra) and the resulting compound has the structure:

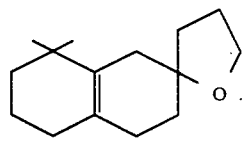

The resulting compound has a strong, persistent, ambergris aroma, with ambergris topnotes with the strength on a scale of 1 to 10 being "10" and the persistence on a scale of 1 to 10 being "10".

EXAMPLE II

Preparation of 3',4,4',5,5',6',7',8'-Octahydro-8',8'-Dimethyl Spiro[Furan-2(3H), 2'(1'H)-Napthalene]

Reactions:

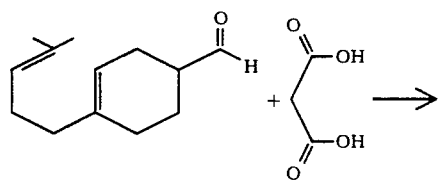

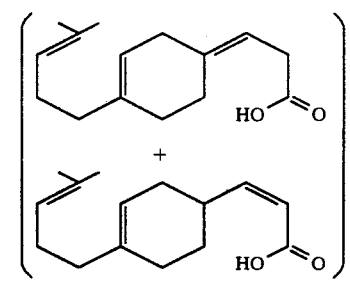

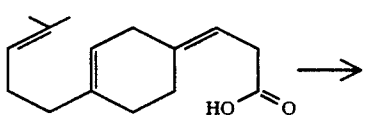

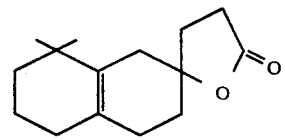

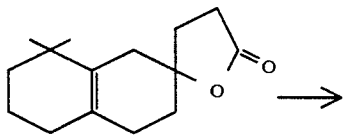

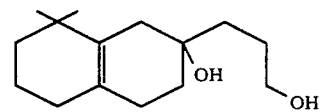

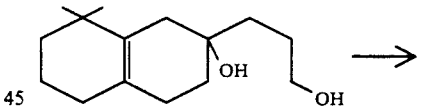

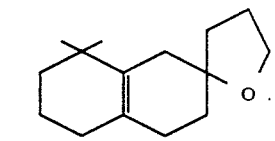

Into a 3 liter reaction vessel equipped with stirrer, thermometer, heating mantle and addition funnel are placed 576 grams (3 moles) of myrac aldehyde having the structure:

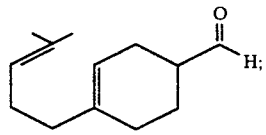

450 grams of malonic acid having the structure:

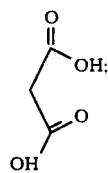

and 800 grams triethyl amine.

The reaction mass is heated with stirring to 85° C. and maintained at 85° C. for a period of 13 hours. GLC analysis indicated unreacted myrac aldehyde.

Thus, an additional 73 grams of malonic acid was added to the reaction mass and the reaction mass was heated at 85° C. for an additional seven hours.

The triethyl amine is then distilled off until the reaction mass distills at 110° C.

The reaction mass is cooled and 900 grams of toluene is added followed by 500 grams of water. The reaction mass is stirred and is now existing in two phases; an organic phase and an aqueous phase. The organic phase is separated from the aqueous phase and the organic phase is washed with 500 grams of 5% aqueous hydrochloric acid.

The tetrahydrofuran is then distilled from the organic phase of the reaction mass until the reaction mass boils at 110° C. The remaining water is then distilled using a Bidwell trap. 5.2 Grams of methane sulphonic acid is then added to the reaction mass. The reaction mass is refluxed at 114° C. for a period of six hours. An additional 5.2 grams of methane sulphonic acid is added and the reaction mass is refluxed for an additional 25 hours. An additional 5 grams of methane sulphonic acid is added to the reaction mass and the reaction mass is distilled for an additional 10 hours. An additional 5 grams of methane sulphonic acid is added and the reaction mass is distilled for an additional 20 hours. GLC analysis indicates 50% conversion.

The reaction mass is then admixed with a 5% sodium bicarbonate aqueous solution (500 grams). The reaction mass is then washed with two 250 volumes of water followed by one 500 gram volume of 5% acetic acid (pH=4.5).

The reaction mass is stripped and distilled through a 12" Vigreux column yielding the following fractions:

| Fraction No. | Vapor Temp. (°C.) | Liquid Temp. (°C.) | Vacuum mm/Hg. Pressure |
|---|---|---|---|
| 1 | 152 | 182 | 1.7 |
| 2-6 | 159-164 | 190-197 | 1.6 |
| 7 | 175 | 212 | 2.0 |
| 8-10 | 177-194 | 212-250 | 3.0. |

Fractions 2-6 are bulked. Fractions 2-6 contain the lactone having the structure:

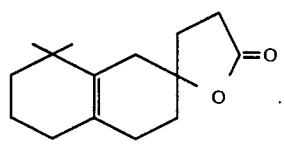

Into a 2 liter reaction vessel equipped with stirrer, thermometer and reflux condenser is placed a solution containing one mole of lithium aluminum hydride in 800 ml tetrahydrofuran. The resulting solution is heated to reflux. Over an one hour period, 266 grams of bulked distillation fractions 2-6, supra, containing the lactone having the structure:

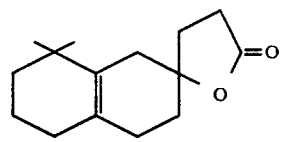

is added to the reaction mass. The reaction mass is refluxed for a period of five hours. Over a period of 0.5 hours 75 grams of ethyl acetate is then added to the reaction mass together with 75 grams of tetrahydrofuran. The resulting reaction mass is refluxed for a period of one hour. Solvents are then distilled from the reaction mass until the temperature of the reaction mass is 68° C.-73° C. (weight of distillate: 637 grams).

The reaction mass is then cooled to 30° C. and 336 grams of potassium hydroxide dissolved in 1000 grams of water is then added to the reaction mass. The reaction mass is then heated to 60° C. and over a period of one hour, 382 grams (2 moles) of para toluene sulphonyl chloride is added to the reaction mass.

The reaction mass is refluxed for a period of five hours at 79° C. The reaction mass is then transferred to a 5 liter separatory funnel and 1 liter of water is added into the separatory funnel under cooling (about 20° C.). 300 Grams of concentrated hydrochloric acid followed by 500 grams of toluene is then added to the reaction mass. The reaction mass is then extracted with two 150 ml volumes of toluene and the extract is washed with 500 ml water followed by 200 grams concentrated hydrochloric acid. 400 ml Tetrahydrofuran are then added to the reaction mass. The organic phase separates from the aqueous phase and the aqueous phase is extracted with toluene. The toluene extract is combined with the organic phase and the resulting product is washed with one 250 gram volume of 5% sodium acetate followed by one 152 gram volume of 5% aqueous sodium acetate. The reaction mass is then stripped of solvent and distilled yielding 213 grams of distillate containing 62% of the compound having the structure:

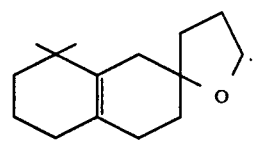

The resulting product is distilled through an 8 plate vigreux column yielding the following fractions:

| Fraction No. | Vapor Temp. (°C.) | Liquid Temp. (°C.) | Vacuum mm/Hg. Pressure |
|---|---|---|---|
| 1 | 87 | 135 | 0.85 |
| 2-5 | 87 | 133 | 0.85 |
| 6 | 86 | 132 | 0.60 |
| 7-11 | 87 | 132-160 | 0.60 |
| 12 | 83 | 160 | 0.60 |
| 13-15 | 108-150 | 160-245 | 0.50. |

Fractions 6-11 contain substantially pure compound having the structure:

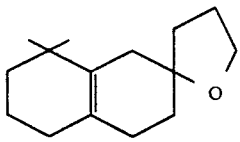

as indicated by NMR and IR analyses.

Bulked fractions 6–11 have a strong persistent ambergris aroma with ambergris topnotes with the strength and persistence being at a level of "10" on a scale of 1–10.

EXAMPLE III

Preparation of Decahydro Spiro[Furan-2(3H),2'(1'H)-Naphthalene]

Reaction:

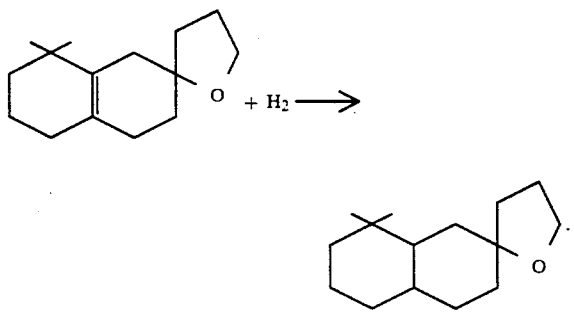

Into a 1 liter zipper autoclave is charged 136 grams of the compound having the structure:

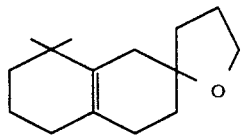

prepared according to Example II; 100 grams of isopropyl alcohol and 1.5 grams of 5% Pd/Al catalyst (K0251 ex Hereaus).

The zipper autoclave is equipped with a hydrogen feed and hydrogen is fed into the autoclave maintaining the temperature at 155° C. and the pressure at 600 psig for a period of 13 hours. The uptake of hydrogen is 1.2 moles.

The autoclave is cooled and opened. The contents are filtered and the solvent is stripped. The resulting product is then distilled through an 8 plate vigreux column yielding the following fractions:

| Fraction No. | Vapor Temp. (°C.) | Liquid Temp. (°C.) | Vacuum mm/Hg. Pressure |
|---|---|---|---|
| 1 | 91 | 136 | 1.45 |
| 2–4 | 97 | 135 | 1.35 |
| 5 | 94 | 135 | 1.65 |
| 6–8 | 98 | 135–146 | 1.0 |
| 9 | 100 | 147 | 1.0 |
| 10 | 95 | 155 | 1.5 |
| 11 | 107 | 184 | 1.6 |
| 12–13 | 240 | 184–220 | 1.6 |

Fractions 6–8 are bulked. Fractions 6–8 has a strong persistent, ambery, tobacco, woody and animalic aroma, with woody, sweet and cigar box-like topnotes. The resulting product of Fractions 6–8 has the structure:

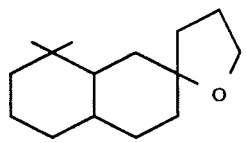

as analyzed by NMR and IR analyses the spectra for which are shown, supra.

EXAMPLE IV

Perfume Formulations

The following woody cologne perfume formulations are prepared:

| Ingredients | Parts by Weight | | |
|---|---|---|---|
| | IV(A) | IV(B) | IV(C) |
| Bergamot oil | 150 | 150 | 150 |
| Orange oil | 200 | 200 | 200 |
| Lemon oil | 50 | 50 | 50 |
| Eugenol | 10 | 10 | 10 |
| 4-(4-methyl-4-hydroxy amyl)-$\Delta^3$cyclohexane carboxaldehyde (LYRAL ® Trademark of International Flavors & Fragrances Inc. of New York, New York) | 40 | 40 | 40 |
| Ylang oil | 2 | 2 | 2 |
| Petigrain Paraguay | 10 | 10 | 10 |
| Gamma-Methyl ionone | 20 | 20 | 20 |
| Vetiver Venezuela | 18 | 18 | 18 |
| 3-Alpha-Methyl-dodecahydro-6,6,9a-trimethyl-napthol[2,1-b]furan | 5 | 5 | 5 |
| Product produced by the reaction of acetic anhydride, polyphosphoric acid and 1,5,9-trimethyl cyclododecatriene-1,5,9 according to the process of Example I of U.S. Pat. No. 3,718,698, the specification for which is incorporated by reference herein | 50 | 50 | 50 |
| Octahydro-9,9-dimethyl 1,6-methanonaphthalene-1-[2H]-ol produced according to Example III of U.S. Pat. No. 3,996,169, the specification for which is incorporated by reference herein | 50 | 50 | 50 |
| The compound having the structure: 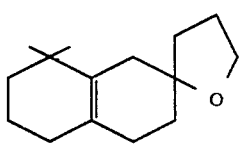 prepared according to Example II, supra, bulked distillation fractions 6–11. | 12 | 0 | 0 |
| The compound having the structure: | 0 | 12 | 0 |

| Ingredients | Parts by Weight | | |
|---|---|---|---|
| | IV(A) | IV(B) | IV(C) |
| 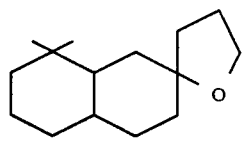produced according to Example III, supra, bulked distillation fractions 6-8. | | | |
| 50:50 (wt:wt) Mixture of the compound having the structure: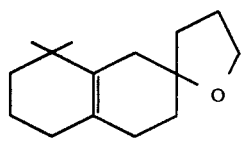prepared according to Example II, bulked distillation fractions 6-11 and the compound having the structure: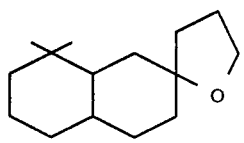produced according to Example III, bulked distillation fractions 6-8. | 0 | 0 | 12 |

The compound having the structure:

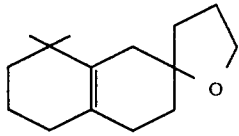

prepared according to Example II, imparts to this woody cologne formulation strong, persistent, ambergris undertones and strong, persistent ambergris topnotes. Accordingly, the perfume composition of Example IV(A) can be described as "a woody cologne aroma, with strong, persistent, ambergris undertones and strong, persistent, ambergris topnotes".

The compound having the structure:

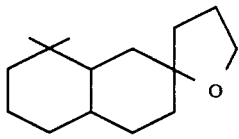

prepared according to Example III, bulked distillation fractions 6-8 imparts to this woody cologne formulation strong, persistent, ambery, tobacco, woody and animalic undertones, with woody, sweet and cigar box-like topnotes. Accordingly, the perfume composition of Example IV(B) can be described as "a woody cologne aroma, with strong, persistent, ambery, tobacco, woody and animalic undertones, with woody, sweet and cigar box-like topnotes".

The combination of the compounds having the structures:

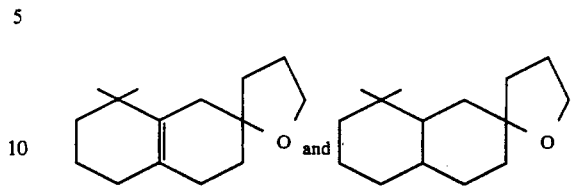

imparts to this woody cologne formulation strong, persistent, ambergris, ambery, tobacco, woody and animalic undertones, with strong, persistent, ambergris, woody, sweet and cigar box-like topnotes. Accordingly, the perfume composition of Example IV(C) can be described as "a woody cologne aroma with strong, persistent, ambergris, ambery, tobacco, woody and animalic undertones, and ambergris, woody, sweet and cigar box-like topnotes".

EXAMPLE V

Preparation of Cosmetic Powder Composition

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
|---|---|
| The compound having the structure: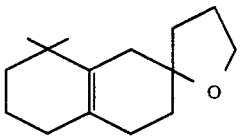prepared according to Example II, bulked distillation fractions 6-11. | A strong, persistent, ambergris aroma, with ambergris topnotes. |
| Compound having the structure: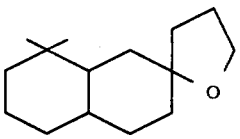prepared according to Example III, bulked distillation fractions 6-8. | A strong, persistent, ambery, tobacco, woody and animalic aroma, with woody, sweet and cigar box-like topnotes. |
| Perfume composition of Example IV(A). | A woody cologne aroma, with strong, persistent, ambergris undertones and strong, persistent, ambergris topnotes. |
| Perfume composition of Example IV(B). | A woody cologne aroma, with strong, persistent, ambery, tobacco, woody and animalic undertones, with woody, sweet and cigar box-like topnotes. |
| Perfume composition of Example IV(C). | A woody cologne aroma with strong, persistent, ambergris, ambery, tobacco, woody and animalic undertones and ambergris, woody, sweet and cigar box-like topnotes. |

EXAMPLE VI

Perfumed Liquid Detergents

Concentrated liquid detergents (Lysine salt of n-dodecylbenzene sulfonic acid as more specifically described in U.S. Pat. No. 3,948,818 issued on Apr. 6, 1976 incorporated by reference herein) with aroma nuances as set forth in Table II of Example V are prepared containing 0.10%, 0.15%, 0.20%, 0.25%, 0.30% and 0.35% of the substance set forth in Table II of Example V. They are prepared by adding and homogeneously mixing the appropriate quantity of substance set forth in Table II of Example V in the liquid detergent. The detergents all possess excellent aromas as set forth in Table II of Example V, the intensity increasing with greater concentrations of substances as set forth in Table II of Example V.

EXAMPLE VII

Preparation of Colognes and Handkerchief Perfumes

Compositions as set forth in Table II of Example V are incorporated into colognes at concentrations of 2.0%, 2.5%, 3.0%, 3.5%, 4.0%, 4.5% and 5.0% in 80%, 85%, 90% and 95% aqueous food grade ethanol solutions; and into handkerchief perfumes at concentrations of 15%, 20%, 25% and 30% (in 80%, 85%, 90% and 95% aqueous food grade ethanol solutions). Distinctive and definitive fragrances as set forth in Table II of Example V are imparted to the colognes and to the handkerchief perfumes at all levels indicated.

EXAMPLE VIII

Preparation of Soap Compositions

One hundred grams of soap chips [per sample]-(IVORY ® produced by the Procter & Gamble Company of Cincinnati, Ohio), are each mixed with one gram samples of substances as set forth in Table II of Example V until homogeneous compositions are obtained. In each of the cases, the homogeneous compositions are heated under 8 atmospheres pressure at 180° C. for a period of three hours and the resulting liquids are placed into soap molds. The resulting soap cakes, on cooling manifest aromas as set forth in Table II of Example V.

EXAMPLE IX

Preparation of Solid Detergent Compositions

Detergents are prepared using the following ingredients according to Example I of Canadian Patent No. 1,007,948 (incorporated by reference herein):

| Ingredient | Percent by Weight |
| --- | --- |
| "NEODOL" ® 45-11 (a $C_{12}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a phosphate-free detergent. Samples of 100 grams each of this detergent are admixed with 0.10, 0.15, 0.20 and 0.25 grams of each of the substances as set forth in Table II of Example V. Each of the detergent samples has an excellent aroma as indicated in Table II of Example V.

EXAMPLE X

Utilizing the procedure of Example I at column 15 of U.S. Pat. No. 3,632,396 (the disclosure of which is incorporated herein by reference), non-woven cloth substrates useful as drier-added fabric softening articles of manufacture are prepared wherein the substrate, the substrate coating, the outer coating and their perfuming material are as follows:

1. A water "dissolvable" paper ("Dissolvo Paper");
2. Adogen 448 (m.p. about 140° F.) as the substrate coating; and
3. An outer coating having the following formulation (m.p. about 150° F.):
   57%—$C_{20\text{-}22}$ HAPS;
   22%—isopropyl alcohol;
   20%—antistatic agent; and
   1%—of one of the substances as set forth in Table II of Example V.

Fabric softening compositions prepared according to Example I at column 15 of U.S. Pat. No. 3,632,396 having the aroma characteristics as set forth in Table II of Example V, supra, consist of a substrate coating having a weight of about 3 grams per 100 square inches of substrate, a first coating located directly on the substrate coating consisting of about 1.85 grams per 100 square inches of substrate; and an outer coating coated on the first coating consisting of about 1.4 grams per 100 square inches of substrate. One of the substances of Table II of Example V is admixed in each case with the outer coating mixture, thereby providing a total aromatized outer coating weight ratio to substrate of about 0.5:1 by weight of the substrate. The aroma characteristics are imparted in a pleasant manner to the head space in a dryer on operation thereof in each case using said drier-added fabric softener non-woven fabrics and these aroma characteristics are described in Table II of Example V, supra.

EXAMPLE XI

Hair Spray Formulations

The following hair spray formulation is prepared by first dissolving PVP/VA E-735 copolymer manufactured by the GAF Corporation of 140 West 51st Street, New York, N.Y., in 91.62 grams of 95% of food grade ethanol. 8.0 Grams of the polymer is dissolved in the alcohol. The following ingredients are added to the PVP/VA alcoholic solution:

| Ingredient | Percent by Weight |
| --- | --- |
| Dioctyl sebacate | 0.05 |
| Benzyl alcohol | 0.10 |
| Dow Corning 473 fluid (prepared by the Dow Corning Corporation) | 0.10 |
| TWEEN ® 20 surfactant (prepared by ICI America Corporation | 0.03 |
| One of the perfumery substances as set forth in Table II of Example V, supra. | 0.10 |

The perfuming substances as set forth in Table II of Example V add aroma characteristics as set forth in Table II of Example V which are rather intense and aesthetically pleasing to the users of the soft-feel, good-hold pump hair sprays.

EXAMPLE XII

Conditioning Shampoos

Monamid CMA (prepared by the Mona Industries Company)(3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation)(1.4 weight percent). The resulting melt is admixed with Stepanol WAT produced by the Stephan Chemical Company (35.0 weight percent). The resulting mixture is heated to 60° C. and mixed until a clear solution is obtained (at 60° C.). This material is "COMPOSITION A".

GAFQUAT® 755N polymer (manufactured by GAF Corporation of 140 West 51st Street, New York, N.Y.)(5.0 weight percent) is admixed with 0.1 weight percent sodium sulfite and 1.4 weight percent polyethylene glycol 6000 distearate produced by Armak Corporation. This material is "COMPOSITION B".

The resulting "COMPOSITION A" and "COMPOSITION B" are then mixed in a 50:50 weight ratio of A:B and cooled to 45° C. and 0.3 weight percent of perfuming substance as set forth in Table II of Example V is added to the mixture. The resulting mixture is cooled to 40° C. and blending is carried out for an additional one hour in each case. At the end of this blending period, the resulting material has a pleasant fragrance as indicated in Table II of Example V.

What is claimed is:

1. A compound having a structure selected from the group consisting of:

(i)

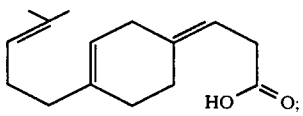

(ii)

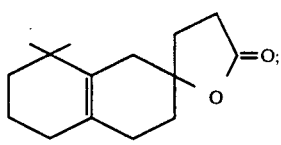

and
(iii)

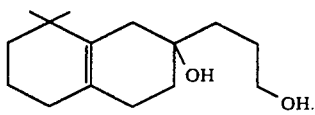

2. A process for preparing the polyhydrodimethyl-naphthalene spirofuran derivative of claim 1 comprising carrying out the reactions in sequence:

(i)

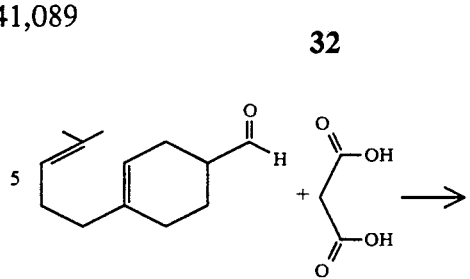

(ii)

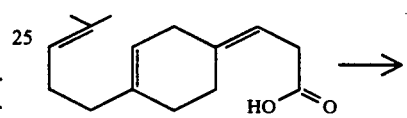

(iii)

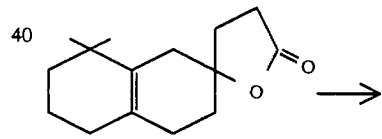

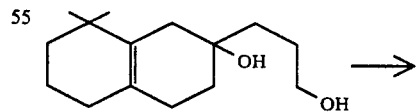

and
(iv)

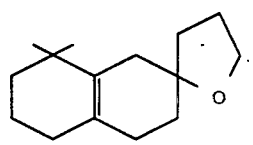

3. The process of claim 2 comprising the additional step of carrying out the reaction:

33
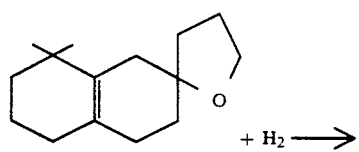 + H₂ ⟶
34
-continued
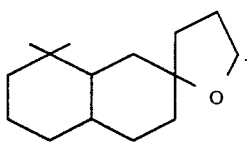
* * * * *